United States Patent
Chou et al.

(12) 
(10) Patent No.: US 10,538,472 B1
(45) Date of Patent: Jan. 21, 2020

(54) EXTRACTION PROCESS FOR HIGH-BOILING ALDEHYDE PRODUCT SEPARATION AND CATALYST RECOVERY

(71) Applicant: DAIREN CHEMICAL CORPORATION, Taipei (TW)

(72) Inventors: June-Yen Chou, Taipei (TW); Hsing-Yun Wang, Taipei (TW); Shih-Feng Chiu, Taipei (TW)

(73) Assignee: Dairen Chemical Corporation, Taipei (TW)

( * ) Notice: Subject to any disclaimer, the term of this patent is extended or adjusted under 35 U.S.C. 154(b) by 0 days.

(21) Appl. No.: 16/276,237

(22) Filed: Feb. 14, 2019

(51) Int. Cl.
*C07C 45/50* (2006.01)
*B01D 11/00* (2006.01)
*C07C 45/80* (2006.01)
*B01D 11/04* (2006.01)
*C07C 47/347* (2006.01)

(52) U.S. Cl.
CPC .......... *C07C 45/80* (2013.01); *B01D 11/0492* (2013.01); *C07C 47/347* (2013.01)

(58) Field of Classification Search
CPC ....... C07C 45/50; C07C 45/80; C07C 47/347; B01D 11/0492
See application file for complete search history.

(56) References Cited

U.S. PATENT DOCUMENTS

| | | | |
|---|---|---|---|
| 4,845,306 | A | 7/1989 | Puckette |
| 5,138,101 | A | 8/1992 | Devon |
| 6,365,782 | B1 | 4/2002 | Nakamura et al. |
| 6,376,641 | B2 | 4/2002 | Nagai et al. |
| 6,939,997 | B2 | 9/2005 | Lappe et al. |
| 7,015,362 | B2 | 3/2006 | Lappe et al. |
| 7,301,057 | B2 | 11/2007 | Dukat et al. |
| 8,697,210 | B2 | 4/2014 | Stenson et al. |
| 9,030,762 | B2 | 5/2015 | Minezaki et al. |
| 9,187,213 | B2 | 11/2015 | Prouvost et al. |
| 9,274,252 | B2 | 3/2016 | Kato et al. |
| 2009/0171125 | A1 | 7/2009 | Shih et al. |

FOREIGN PATENT DOCUMENTS

| | | |
|---|---|---|
| EP | 1065194 B2 | 3/2007 |
| JP | 2001010999 A | 1/2001 |
| JP | 2001011008 A | 1/2001 |
| JP | 2001163824 A | 6/2001 |

*Primary Examiner* — Sikarl A Witherspoon

(74) *Attorney, Agent, or Firm* — Nixon Peabody LLP; Thomas Pavelko

(57) ABSTRACT

The invention relates to an extraction process for the recovery of high-boiling aldehyde products and catalysts from a hydroformylation product solution.

21 Claims, No Drawings

EXTRACTION PROCESS FOR HIGH-BOILING ALDEHYDE PRODUCT SEPARATION AND CATALYST RECOVERY

FIELD OF THE INVENTION

The present disclosure relates to an extraction process for the recovery of high-boiling aldehyde products and catalysts from a hydroformylation product solution.

BACKGROUND

All publications herein are incorporated by reference to the same extent as if each individual publication or patent application was specifically and individually indicated to be incorporated by reference. The following description includes information that may be useful in understanding the invention. It is not an admission that any of the information provided herein is prior art or relevant to the presently claimed invention, or that any publication specifically or implicitly referenced is prior art.

Hydroformylation is known in the art as a catalytic method for the conversion of an olefin to an aldehyde, wherein the aldehyde has one more carbon than the starting olefin by the addition of a formyl group (CHO) and a hydrogen atom to the carbon-carbon double bond of the olefin. As a result, the molecular weight and the boiling point of the resulting aldehyde are increased relative to the starting olefin. If the olefin contains more than one carbon-carbon double bond, a formyl group (CHO) and a hydrogen atom may be added to each carbon-carbon double bond of the olefin As is known in the art, the process of hydroformylation requires the use of one or more expensive catalysts. Therefore, in order to reduce catalyst loss, it is advantageous to recover the catalyst from the hydroformylation process. Distillation is often used to recover the hydroformylation catalyst from the hydroformylation process by separating the hydroformylation catalyst from the aldehyde product. During distillation the product stream containing the aldehyde product is heated to a gas so as to separate the aldehyde product from the hydroformylation catalyst. When the boiling point of the aldehyde product is high, a high distillation temperature is needed to obtain good separation efficiency between the aldehyde product and the hydroformylation catalyst. Unfortunately, high distillation temperatures damage the catalyst making it unsuitable for use in subsequent hydroformylation reactions, thereby leading to an increase in catalyst loss.

Methods are known in the art for producing high-boiling point aldehydes. For example, U.S. Pat. No. 6,365,782 B1 describes a hydroformylation process for preparing tricyclodecane dicarbaldehyde and/or pentacyclopentadecane dicarbaldehyde, wherein the tricyclodecane dicarbaldehyde and/or pentacyclopentadecane dicarbaldehyde in the hydroformylation product liquid are extracted with a polyhydric alcohol. However, as discussed therein the dialdehydes react with the polyhydric alcohol used as the extraction solvent to form high-boiling point acetals. The formation of the acetals reduces the yields of the dialdehydes, and in addition, extremely reduces the reaction rate of hydrogenation for producing tricyclodecane dimethanol and pentacyclopentadecane dimethanol, thereby resulting in poor productivity. Further, since the boiling points of the acetals are so close to those of tricyclodecane dimethanol and pentacyclopentadecane dimethanol, they cannot be separated by distillation. To reduce the amount of acetal formation, the addition of one or more tertiary amines was required as described therein.

While methods are known in the art for the preparation of high-boiling point aldehydes by hydroformylation of olefins in the presence of various catalytic systems, further improvements are needed to address various problems associated with separating the high-boiling point aldehyde products from a hydroformylation product solution containing the hydroformylation catalyst, while also reducing the formation of unwanted acetal compounds, particularly without the need to use other substances, such as tertiary amines for reducing the amount of acetal formation. The present invention addresses these needs.

SUMMARY OF THE INVENTION

The following embodiments and aspects thereof are described and illustrated in conjunction with systems, articles of manufacture, compositions, and processes which are meant to be exemplary and illustrative, not limiting in scope.

In various embodiments, the present invention provides a process for separating a high-boiling point aldehyde compound from a non-aqueous hydroformylation product solution, comprising the steps of: (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and (b) separating the biphasic mixture of step (a) to obtain: (i) a non-aqueous hydroformylation solvent layer, comprising: the hydroformylation catalyst, and the non-aqueous hydroformylation solvent; and (ii) an aqueous extraction solvent layer, comprising: the high-boiling point aldehyde compound, and the aqueous extraction solvent.

In some embodiments, the primary alcohol is a $C_1$-$C_3$ primary alcohol.

In some embodiments, the primary alcohol is selected from methanol, ethanol, and n-propanol.

In some embodiments, the primary alcohol is selected from methanol and ethanol.

In some embodiments, the polyalcohol is selected from the group consisting of a branched polyalcohol, monocyclic polyalcohol, and polycyclic polyalcohol.

In some embodiments, the polyalcohol is selected from the group consisting of $C_4$-$C_{20}$ branched polyalcohol, $C_4$-$C_{20}$ monocyclic polyalcohol, and $C_4$-$C_{20}$ polycyclic polyalcohol.

In some embodiments, the polyalcohol is a compound of Formula (I):

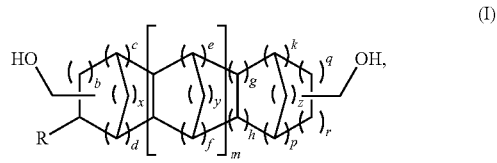

(I)

wherein,
R is selected from H and $CH_3$; x is an integer selected from 0 and 1; y is an integer selected from 0 and 1; z is an integer selected from 0 and 1; b is an integer selected from 0 and 1;

c is an integer selected from 0 and 1; d is an integer selected from 0 and 1; e is an integer selected from 0 and 1; f is an integer selected from 0 and 1; g is an integer selected from 0 and 1; h is an integer selected from 0 and 1; k is an integer selected from 0 and 1; p is an integer selected from 0 and 1; q is an integer selected from 0 and 1; r is an integer selected from 0 and 1; and m is an integer selected from 0 and 1.

In some embodiments, the polyalcohol is selected from the group consisting of 2-methyl-1,3-propanediol; a compound of Formula (II):

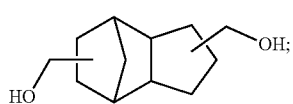

(II)

a compound of Formula (III):

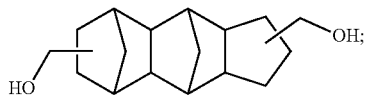

(III)

a compound of Formula (IV):

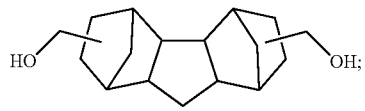

(IV)

and a compound of Formula (V):

(V)

In some embodiments, the polyalcohol is selected from the group consisting of 2-methyl-1,3-propanediol; 1,1-cyclohexanedimethanol; 1,2-cyclohexanedimethanol; 1,3-cyclohexanedimethanol; 1,4-cyclohexanedimethanol; 3,8-bis(hydroxymethyl)tricyclo[5.2.1.0$^{2-6}$]decane; 3,9-bis(hydroxymethyl)tricyclo[5.2.1.0$^{2-6}$]decane; 4,8-bis(hydroxymethyl)tricyclo[5.2.1.0$^{2-6}$]decane; 4,9-bis(hydroxymethyl)tricyclo[5.2.1.0$^{2-6}$]decane; 5,8-bis(hydroxymethyl)tricyclo[5.2.1.0$^{2-6}$]decane; 5,9-bis(hydroxymethyl)tricyclo[5.2.1.0$^{2-6}$]decane; 4,10-bis(hydroxymethyl)pentacyclo[6.5.1.1$^{3-6}$.0$^{2-7}$.0$^{9-13}$]pentadecane; 4,11-bis(hydroxymethyl)pentacyclo[6.5.1.1$^{3-6}$.0$^{2-7}$.0$^{9-13}$]pentadecane; 4,12-bis(hydroxymethyl)pentacyclo[6.5.1.1$^{3-6}$.0$^{2-7}$.0$^{9-13}$]pentadecane; 5,10-bis(hydroxymethyl)pentacyclo[6.5.1.1$^{3-6}$.0$^{2-7}$.0$^{9-13}$]pentadecane; 5,11-bis(hydroxymethyl)pentacyclo[6.5.1.1$^{3-6}$.0$^{2-7}$.0$^{9-13}$]pentadecane; 5,12-bis(hydroxymethyl)pentacyclo[6.5.1.1$^{3-6}$.0$^{2-7}$.0$^{9-13}$]pentadecane; 5,12-bis(hydroxymethyl)pentacyclo[9.2.1.1$^{4-7}$.0$^{2-10}$.0$^{3-8}$]pentadecane; 5,13-bis(hydroxymethyl)pentacyclo[9.2.1.1$^{4-7}$.0$^{2-10}$.0$^{3-8}$]pentadecane; 6,12-bis(hydroxymethyl)pentacyclo[9.2.1.1$^{4-7}$.0$^{2-10}$.0$^{3-8}$]pentadecane; and 6,13-bis(hydroxymethyl)pentacyclo[9.2.1.1$^{4-7}$.0$^{2-10}$.0$^{3-8}$]pentadecane.

In some embodiments, the polyalcohol is about 10% to about 80% by weight, the primary alcohol is about 10% to about 70% by weight, and the water is about 5% to about 30% by weight, based on the total weight of the aqueous extraction solvent.

In some embodiments, the high-boiling point aldehyde compound has a boiling point of at least about 100° C. at atmospheric pressure.

In some embodiments, the high-boiling point aldehyde compound is a compound of Formula (VI):

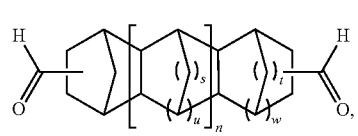

(VI)

wherein, s is an integer selected from 0 and 1; t is an integer selected from 0 and 1; u is an integer selected from 0 and 1; w is an integer selected from 0 and 1; and n is an integer selected from 0 and 1.

In some embodiments, the high-boiling point aldehyde compound is selected from the group consisting of a compound of Formula (VII):

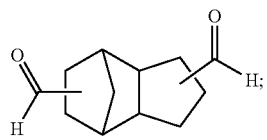

(VII)

a compound of Formula (VIII):

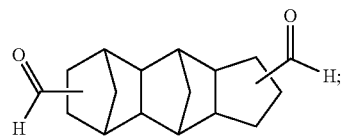

(VIII)

and a compound of Formula (IX):

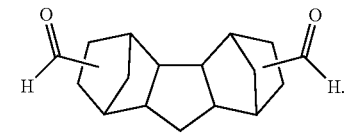

(IX)

In some embodiments, the step of contacting the non-aqueous hydroformylation product solution with the aqueous extraction solvent to form the biphasic mixture is performed at a temperature of about 25° C. to about 75° C.

In some embodiments, the process further comprises recovering the hydroformylation catalyst from the non-aqueous hydroformylation solvent layer.

In some embodiments, the hydroformylation catalyst comprises a hydroformylation catalyst component and a ligand.

In some embodiments, the hydroformylation catalyst component comprises an active material.

In some embodiments, the active material is at least one selected from rhodium and cobalt.

In some embodiments, the process further comprises subjecting the aqueous extraction solvent layer to catalytic hydrogenation, thereby converting the high-boiling point aldehyde compound into corresponding high-boiling point alcohol compound.

In some embodiments, the aqueous extraction solvent layer has a pH value of less than about 7.

In some embodiments, the aqueous extraction solvent layer has a viscosity of less than or equal to about 100 centipoise (cP) at about 25° C.

In various embodiments, the present invention provides an aldehyde product composition obtained by a process, comprising the steps of: (a) contacting a non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises a high-boiling point aldehyde compound, a hydroformylation catalyst, and a non-aqueous hydroformylation solvent; and (b) separating the biphasic mixture of step (a) to obtain: (i) a non-aqueous hydroformylation solvent layer, comprising: the hydroformylation catalyst, and the non-aqueous hydroformylation solvent; and (ii) an aqueous extraction solvent layer, comprising: the aldehyde product composition and the aqueous extraction solvent, wherein the aldehyde product composition comprises the high-boiling point aldehyde compound and an acetal compound.

In some embodiments, a weight ratio of the high-boiling point aldehyde compound to the acetal compound is about 1:0.0001 to about 1:0.05.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

One skilled in the art will recognize many methods and materials similar or equivalent to those described herein, which could be used in the practice of the invention. Other features and advantages of the invention will become apparent from the following detailed description. Indeed, the invention is in no way limited to the methods and materials described. For convenience, certain terms employed herein, in the specification, examples and appended claims are collected here.

As used herein the term "comprising" or "comprises" is used in reference to compositions, methods, processes, articles of manufacture, systems, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All processes described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

The term "about" as used herein means plus/minus 20% of the stated value. For example, about 75° C. encompasses the range of 60° C. to 90° C.

The term "high-boiling point alcohol compound" as used herein means the alcohol compound obtained following hydrogenation of the corresponding high-boiling point aldehyde compound.

The terms "dialdehyde" and "dialdehyde compound" as used herein mean a compound containing two aldehyde groups.

The terms "monoaldehyde" and "monoaldehyde compound" as used herein mean a compound containing one aldehyde group.

The terms "dialcohol" and "dialcohol compound" as used herein mean a compound containing two hydroxyl groups.

The terms "polyalcohol" and "polyhydric alcohol" are used interchangeably herein to mean a compound containing two or more hydroxyl groups.

The terms "tricyclodecane dialdehyde" and "tricyclodecane dicarbaldehyde" refer to a compound of Formula (VII):

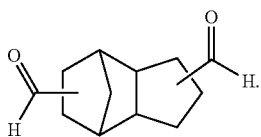
(VII)

The terms "pentacyclopentadecane dialdehyde" and "pentacyclopentadecane dicarbaldehyde" refer to a compound of Formula (VIII):

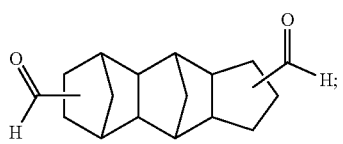
(VIII)

a compound of Formula (IX):

(IX)

and combinations thereof.

The term "tricyclodecane dimethanol" refers to a compound of Formula (II):

(II)

The term "pentacyclopentadecane dimethanol" refers to a compound of Formula (III):

(III)

a compound of Formula (IV):

(IV)

and combinations thereof.

Synthetic Preparation. In various embodiments, compounds, compositions, formulations, articles of manufacture, reagents, products, etc. of the invention as disclosed herein may be synthesized using any synthetic method available to one of skill in the art. In various embodiments, the compounds, compositions, formulations, articles of manufacture, reagents, products, etc. of the invention disclosed herein can be prepared in a variety of ways known to one skilled in the art of organic synthesis, and in analogy with the exemplary compounds, compositions, formulations, articles of manufacture, reagents, products, etc. whose synthesis is described herein. The starting materials used in preparing these compounds, compositions, formulations, articles of manufacture, reagents, products, etc. may be commercially available or prepared by known methods. Preparation of compounds, can involve the protection and deprotection of various chemical groups. The need for protection and deprotection, and the selection of appropriate protecting groups can be readily determined by one skilled in the art. The chemistry of protecting groups can be found, for example, in Greene and Wuts, Protective Groups in Organic Synthesis, $4^{th}$. Ed., Wiley & Sons, 2006, which is incorporated herein by reference in its entirety. Non-limiting examples of synthetic methods used to prepare various embodiments of compounds, compositions, formulations, articles of manufacture, reagents, products, etc. of the invention are disclosed in the Examples section herein.

The inventors discovered that aldehyde product compositions and/or high-boiling point aldehyde compounds may be extracted and/or separated and/or obtained from a non-aqueous hydroformylation product solution, wherein the non-aqueous hydroformylation product solution comprises a high-boiling point aldehyde compound, hydroformylation catalyst, and non-aqueous hydroformylation solvent, by contacting the non-aqueous hydroformylation product solution with an aqueous extraction solvent to form a biphasic mixture (2 phase mixture), wherein the aqueous extraction solvent comprises at least one polyalcohol, at least one primary alcohol, and water. The biphasic mixture is separated into 2 phases: (i) a non-aqueous hydroformylation solvent layer (i.e., a nonpolar phase), comprising: the hydroformylation catalyst and non-aqueous hydroformylation solvent; and (ii) an aqueous extraction solvent layer (i.e. a polar phase), comprising: the aldehyde product composition and/or high-boiling point aldehyde compound. In various embodiments of the present invention the high-boiling point aldehyde compounds are extracted and/or separated and/or obtained from the non-aqueous hydroformylation product solution at a temperature less than or equal to about 75° C., and with essentially none or minimal amounts of acetal compound formation.

In various embodiments, the processes of the present invention may be employed for the recovery of aldehydes (e.g., high-boiling point aldehyde compounds) which have a boiling point greater than about 100° C. (at atmospheric pressure) and thus cannot be easily removed as a vapor from the hydroformylation reactor (for example by distillation procedures). In various embodiments, the processes of the present invention may be operated in a manner whereby essentially none or minimal amounts of the hydroformylation catalysts and/or hydroformylation catalyst components (e.g., a complex rhodium or cobalt compound) and/or ligand, is extracted by the aqueous extraction solvent (e.g., polyalcohol:primary alcohol:water solution) into the aqueous extraction solvent layer. Thus, the extraction/separation processes of the present invention results in high yield and/or recovery of the aldehyde product composition and/or high-boiling point aldehyde compounds without any significant loss of hydroformylation catalyst and/or hydroformylation catalyst components and/or ligand from the hydroformylation production system. Moreover, since the separation/extraction of the high-boiling point aldehyde compound is performed at temperatures at or below about 75° C., the amount of acetal compound formed is minimized.

In various embodiments, the non-aqueous hydroformylation solvent layer containing the hydroformylation catalyst may be recycled and/or returned to the hydroformylation reactor for subsequent use. In various embodiments, the active materials (e.g., rhodium and/or cobalt) may be recovered and/or recycled from the non-aqueous hydroformylation solvent layer.

In various embodiments, the aqueous extraction solvent layer containing the high-boiling point aldehyde compound may be used as the feed to known hydrogenation or oxidation processes wherein the high-boiling point aldehyde compound may be converted to alcohol, carboxylic acid, or amino derivatives according to known methods as so desired. Alternatively, in various embodiments the high-boiling point aldehyde compound may also be isolated and/or recovered from the polyalcohol:primary alcohol:water solution by various known methods.

Without being bound by theory, in various embodiments the high-boiling point aldehyde compounds which may be recovered or separated in accordance with the present invention comprise aliphatic, including aliphatic aldehyde compounds derived from ethylenically-unsaturated, low molecular weight polymers, alicyclic, aromatic and heterocyclic compounds containing one, two, three or more aldehyde (formyl or carboxaldehyde) groups. In various embodiments, the high-boiling point aldehyde compounds may contain up to 40 carbon atoms and have a boiling point (at atmospheric pressure) of at least about 100° C.

Without being bound by theory, the partitioning of the aldehyde product compositions and/or high-boiling point aldehyde compounds between the non-aqueous hydroformylation solvent layer and the aqueous extraction solvent layer is an equilibration process. The relative volumes of aqueous extraction solvent and non-aqueous hydroformylation product solution is determined by the solubility of the various aldehyde product compositions and/or high-boiling point aldehyde compounds in the particular combination of solutions being utilized, the polyalcohol:primary alcohol:water content of the aqueous extraction solvent, and how much aldehyde product compositions and/or high-boiling point aldehyde compound is to be removed. For example, without being bound by theory, if the high-boiling point aldehyde compound to be separated has a high solubility in the aqueous extraction solvent and is present in the non-aqueous hydroformylation product solution in a relatively low concentration, a low volume ratio of aqueous extraction solvent to non-aqueous hydroformylation product solution may be used to effect practical extraction of the high-boiling point aldehyde compound. Larger concentrations of the high-boiling point aldehyde compound normally require the use of a higher aqueous extraction solvent:non-aqueous hydroformylation product solution volume ratio to achieve a practical degree of extraction of the high-boiling point aldehyde compound from the non-aqueous hydroformylation product solution. When the high-boiling point aldehyde compound has a low relative solubility in the aqueous extraction solvent, more aqueous extraction solvent per unit volume of non-aqueous hydroformylation product solution may be required. In various embodiments, the volume ratio of aqueous extraction solvent:non-aqueous hydroformylation product solution therefore may vary from about 10:1 to about 1:10. In some embodiments, the volume ratios of aqueous extraction solvent:non-aqueous hydroformylation product solution in the range of about 1:1 to about 1:4 may be used for the recovery of most aldehyde product compositions and/or high-boiling point aldehyde compounds.

The inventors have also discovered that the solubility of the aldehyde product compositions and/or high-boiling point aldehyde compound in the aqueous extraction solvent is higher at lower extraction temperatures. Moreover, the inventors have also discovered that the amount of hydroformylation catalyst loss and/or amount of active material (e.g., rhodium or cobalt) loss is lower at lower extraction temperatures. Additionally, the inventors have also discovered that the amount of acetal compound formed is lower at lower extraction temperatures. Thus, no advantage is achieved by using temperatures greater than those of the hydroformylation reaction temperature, e.g., about 90° C. to about 125° C., and superior results are obtained when the extraction temperature is lower than that of the hydroformylation reactor. In various embodiments, the extraction process (including contacting the non-aqueous hydroformylation product solution with the aqueous extraction solvent to form the biphasic mixture) is carried out at a temperature in the range of about 25° C. to about 75° C.

Without being bound by theory, the time over which the non-aqueous hydroformylation product solution and aqueous extraction solvent are contacted, i.e., prior to phase separation, is dependent upon the speed at which the phases reach equilibrium. In practice this may vary from a minute or less to long mixing times in excess of three hours. In some embodiments, the non-aqueous hydroformylation product solution and aqueous extraction solvent are contacted for less than about 2 hours. In some embodiments, the non-aqueous hydroformylation product solution and aqueous extraction solvent are contacted for about 10 minutes to about 20 minutes.

The mixing time of the non-aqueous hydroformylation product solution and the aqueous extraction solvent is not particularly limited. Persons of skill in the art can adjust the mixing time as appropriate. In some embodiments, the non-aqueous hydroformylation product solution and the aqueous extraction solvent are mixed simultaneously. In some embodiments, the non-aqueous hydroformylation product solution and the aqueous extraction solvent are mixed sequentially.

In some embodiments, the hydroformylation catalyst may optionally be recycled and returned to the hydroformylation reactor zone for use in subsequent hydroformylation reactions.

In some embodiments, the extraction and/or separation processes of the present invention are adaptable so as to be used in continuous, semi-continuous, or batch hydroformylation processes. In some embodiments, the extraction and/or separation processes of the present invention are used in batch hydroformylation processes.

In some embodiments, the high-boiling aldehyde compounds may optionally be converted to alcohol, carboxylic acid, or amino derivatives according to known methods as so desired.

Various abbreviations used herein include: 2-methyl-1,3-propanediol (MPO); methyl ($CH_3$); cyclhexanedimethanol (CHDM); tricyclo[5.2.1.0(2,6)]decanedimethanol (TCDDM); tricyclo[5.2.1.0(2,6)]decanedialdehyde (TCDDA); methanol (MeOH); and ethanol (EtOH).

Non-Limiting Embodiments of the Invention

Processes for Separating a High-Boiling Point Aldehyde Compound from a Non-Aqueous Hydroformylation Product Solution In various embodiments, the present invention provides a process for separating a high-boiling point aldehyde compound from a non-aqueous hydroformylation product solution, comprising the steps of: (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and (b) separating the biphasic mixture of step (a) to obtain: (i) a non-aqueous hydroformylation solvent layer, comprising: the hydroformylation catalyst, and the non-aqueous hydroformylation solvent; and (ii) an aqueous extraction solvent layer, comprising: the high-boiling point aldehyde compound, and the aqueous extraction solvent.

In various embodiments, the present invention provides a process for separating a high-boiling point aldehyde compound from a non-aqueous hydroformylation product solution, comprising the steps of: (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and (b) separating the biphasic mixture of step (a) to obtain: (i) a non-aqueous hydroformylation solvent layer, comprising: the hydroformylation catalyst, and the non-aqueous hydroformylation solvent; and (ii) an aqueous extraction solvent layer, comprising: an aldehyde product composition and the aqueous extraction solvent, wherein the aldehyde product composition comprises the high-boiling point aldehyde compound and an acetal compound.

In various embodiments, the present invention provides a process for separating a high-boiling point aldehyde compound from a non-aqueous hydroformylation product solution, comprising the steps of: (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and (b) separating the biphasic mixture of step (a) to obtain: (i) a non-aqueous hydroformylation solvent layer, comprising: a first portion of the hydroformylation catalyst, and the non-aqueous hydroformylation solvent; and (ii) an aqueous extraction solvent layer, comprising: the high-boiling point aldehyde compound, the aqueous extraction solvent, and a second portion of the hydroformylation catalyst. In some embodiments, the hydroformylation catalyst comprises a hydroformylation catalyst component and a ligand. In some embodiments, the hydroformylation catalyst component comprises an active material. In some embodiments, an amount of the active material in the aqueous extraction solvent layer is less than about 2 ppm.

In various embodiments, the present invention provides a process for separating a high-boiling point aldehyde compound from a non-aqueous hydroformylation product solution, comprising the steps of: (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and (b) separating the biphasic mixture of step (a) to obtain: (i) a non-aqueous hydroformylation solvent layer, comprising: a first portion of the hydroformylation catalyst, and the non-aqueous hydroformylation solvent; and (ii) an aqueous extraction solvent layer, comprising: an aldehyde product composition, the aqueous extraction solvent, and a second portion of the hydroformylation catalyst, wherein the aldehyde product composition comprises the high-boiling point aldehyde compound and an acetal compound.

In some embodiments, the hydroformylation catalyst comprises a hydroformylation catalyst component, and a ligand. In some embodiments, the hydroformylation catalyst component comprises an active material. In some embodiments, an amount of the active material in the aqueous extraction solvent layer is less than about 2 ppm.

In some embodiments, the first portion of the hydroformylation catalyst comprises a hydroformylation catalyst component, and a ligand. In some embodiments, the second portion of the hydroformylation catalyst comprises a hydroformylation catalyst component, and a ligand. In some embodiments, the hydroformylation catalyst component comprises an active material. In some embodiments, an amount of the active material in the aqueous extraction solvent layer is less than about 2 ppm.

In some embodiments, the process further comprises recovering the high-boiling point aldehyde compound from the aqueous extraction solvent layer. In some embodiments, the process further comprises recovering the aldehyde product composition from the aqueous extraction solvent layer, wherein the aldehyde product composition comprises the high-boiling point aldehyde compound, and the acetal compound.

In some embodiments, the step of contacting the non-aqueous hydroformylation product solution with the aqueous extraction solvent to form the biphasic mixture is performed at a temperature of about 25° C. to about 75° C. In some embodiments, the step of contacting the non-aqueous hydroformylation product solution with the aqueous extraction solvent to form the biphasic mixture is performed at a temperature of about 25° C. to about 75° C., about 25° C. to about 70° C., about 25° C. to about 65° C., about 25° C. to about 60° C., about 25° C. to about 55° C., about 25° C. to about 50° C., about 25° C. to about 45° C., about 25° C. to about 40° C., about 25° C. to about 35° C., or about 25° C. to about 30° C. In some embodiments, the step of contacting the non-aqueous hydroformylation product solution with the aqueous extraction solvent to form the biphasic mixture is performed at a temperature of about 25° C. to about 75° C., about 30° C. to about 75° C., about 35° C. to about 75° C., about 40° C. to about 75° C., about 45° C. to about 75° C., about 50° C. to about 75° C., about 55° C. to about 75° C., about 60° C. to about 75° C., about 65° C. to about 75° C., or about 70° C. to about 75° C.

In some embodiments, the process further comprises separating and/or isolating the high-boiling point aldehyde compound from the aldehyde product composition. The separating and/or isolating of the high-boiling point aldehyde compound from the aldehyde product composition may be performed using any known methods.

In some embodiments, the process further comprises separating and/or isolating the hydroformylation catalyst from the non-aqueous hydroformylation solvent layer. The separating and/or isolating the at least one hydroformylation catalyst from the non-aqueous hydroformylation solvent layer may be performed using any known methods.

Non-Aqueous Hydroformylation Product Solution

In various embodiments, the non-aqueous hydroformylation product solution comprises a high-boiling point aldehyde compound, a hydroformylation catalyst, and a non-aqueous hydroformylation solvent.

Non-Aqueous Hydroformylation Solvent Layer

In various embodiments, the non-aqueous hydroformylation solvent layer comprises a hydroformylation catalyst, and a non-aqueous hydroformylation solvent.

In some embodiments, the non-aqueous hydroformylation solvent layer is a nonpolar phase.

In some embodiments, the non-aqueous hydroformylation solvent layer comprises a first portion of the hydroformylation catalyst. In some embodiments, the hydroformylation catalyst comprises a hydroformylation catalyst component, and a ligand, wherein the hydroformylation catalyst component comprises an active material.

Non-Aqueous Hydroformylation Solvents

In various embodiments, the non-aqueous hydroformylation solvent is selected from various alkanes, cycloalkanes, alkenes, cycloalkenes and carbocyclic aromatic compounds. In some embodiments, the non-aqueous hydroformylation solvent is a liquid at standard temperature and pressure. In some embodiments, the non-aqueous hydroformylation solvent has a density which is at least about 0.05 g/mL different from the density of the aqueous extraction solvent employed. In some embodiments, the non-aqueous hydroformylation solvent has a density which is at least about 0.02 g/mL different from the density of the aqueous extraction solvent employed.

Non-limiting examples of non-aqueous hydroformylation solvents include alkane and cycloalkanes such as pentane, hexane, heptane, dodecane, decane, octane, iso-octane mixtures, cyclohexane, cyclooctane, cyclododecane, decalin, methylcyclohexane; aromatic hydrocarbons such as benzene, toluene, xylene isomers, tetralin, cumene, mesitylene, pseudocumene, ethylbenzene, diethylbenzene and triethylbenzene; dichloromethane, trichloromethane, alkyl-substituted aromatic compounds such as the isomers of diisopropylbenzene, triisopropylbenzene, tert-butylbenzene, isopropylbenzene, 1,3-diisopropylbenzene and 1,4-diisopropylbenzene; and crude hydrocarbon mixtures such as naphtha and kerosene. In some embodiments, the non-aqueous hydroformylation solvent is selected from alkanes having 5 to 20 carbon atoms, alkyl substituted benzenes having 9 to 15 carbon atoms, tetrahydronaphthalene, and decahydronaphthalene. In some embodiments, the non-aqueous hydroformylation solvent comprises methylcyclohexane.

Aqueous Extraction Solvent

In various embodiments, the present invention provides an aqueous extraction solvent for extracting a high-boiling point aldehyde compound from a non-aqueous hydroformylation product solution, wherein the aqueous extraction solvent comprises at least one polyalcohol, at least one primary alcohol, and water.

In some embodiments, the polyalcohol is about 10% to about 80% by weight, the primary alcohol is about 10% to about 70% by weight, and the water is about 10% to about 30% by weight, based on the total weight of the aqueous extraction solvent.

In some embodiments, the polyalcohol is about 10% to about 70% by weight, the primary alcohol is about 10% to about 70% by weight, and the water is about 5% to about 30% by weight, based on the total weight of the aqueous extraction solvent.

In some embodiments, the polyalcohol is about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, or about 10% to about 15% by weight, based on the total weight of the aqueous extraction solvent. In some embodiments, the polyalcohol is about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, or about 75% to about 80% by weight, based on the total weight of the aqueous extraction solvent.

In some embodiments, the polyalcohol is about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, or about 10% to about 15% by weight, based on the total weight of the aqueous extraction solvent. In some embodiments, the polyalcohol is about 10% to about 70%, about 15% to about 70%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, or about 65% to about 70% by weight, based on the total weight of the aqueous extraction solvent.

In some embodiments, the primary alcohol is about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, or about 10% to about 15% by weight, based on the total weight of the aqueous extraction solvent. In some embodiments, the primary alcohol is about 10% to about 70%, about 15% to about 70%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, or about 65% to about 70% by weight, based on the total weight of the aqueous extraction solvent.

In some embodiments, the water is about 5% to about 30%, about 5% to about 29%, about 5% to about 28%, about 5% to about 27%, about 5% to about 26%, about 5% to about 25%, about 5% to about 24%, about 5% to about 23%, about 5% to about 22%, about 5% to about 21%, about 5% to about 20%, about 5% to about 19%, about 5% to about 18%, about 5% to about 17%, about 5% to about 16%, about 5% to about 15%, about 5% to about 14%, about 5% to about 13%, about 5% to about 12%, about 5% to about 11%, about 5% to about 10%, about 5% to about 9%, about 5% to about 8%, about 5% to about 7%, or about 5% to about 6% by weight, based on the total weight of the aqueous extraction solvent. In some embodiments, the water is about 5% to about 30%, about 6% to about 30%, about 7% to about 30%, about 8% to about 30%, about 9% to about 30%, about 10% to about 30%, about 11% to about 30%, about 12% to about 30%, about 13% to about 39%, about 14% to about 30%, about 15% to about 30%, about 16% to about 30%, about 17% to about 30%, about 18% to about 30%, about 19% to about 30%, about 20% to about 30%, about 21% to about 30%, about 22% to about 30%, about 23% to about 30%, about 24% to about 30%, about 25% to about 30%, about 26% to about 30%, about 27% to about 30%, about 28% to about 30%, or about 29% to about 30% by weight, based on the total weight of the aqueous extraction solvent.

In some embodiments, the water is about 20% to about 30%, about 20% to about 29%, about 20% to about 28%, about 20% to about 27%, about 20% to about 26%, about 20% to about 25%, about 20% to about 24%, about 20% to about 23%, about 20% to about 22%, or about 20% to about 21% by weight, based on the total weight of the aqueous extraction solvent. In some embodiments, the water is about 20% to about 30%, about 21% to about 30%, about 22% to about 30%, about 23% to about 30%, about 24% to about 30%, about 25% to about 30%, about 26% to about 30%, about 28% to about 30%, or about 29% to about 30% by weight, based on the total weight of the aqueous extraction solvent.

The relative amounts of polyalcohol:primary alcohol:water constituting the aqueous extraction solvent can vary substantially depending, for example, on the particular high-boiling point aldehyde compound to be recovered and the non-aqueous hydroformylation solvent employed. However, the aqueous extraction solvent must contain sufficient water to allow the separation of the non-aqueous hydroformylation solvent and the aqueous extraction solvent into 2 phases (a nonpolar phase and a polar phase).

In some embodiments, the aqueous extraction solvent comprises a weight ratio of polyalcohol:primary alcohol:water, wherein the weight ratio of polyalcohol:primary alcohol:water is (X:Y:Z), wherein X is an integer from 1 to 8; Y is an integer from 1 to 7; and Z is an integer from 1 to 3. In some embodiments, the weight ratio of polyalcohol:primary alcohol:water is (X:Y:Z), wherein X is an integer from 1 to 7; Y is an integer from 1 to 7; and Z is an integer from 2 to 3.

In some embodiments, the extraction solvent is an aqueous extraction solvent. In some embodiments, the aqueous extraction solvent is an aqueous extraction solution.

In some embodiments, the separation/extraction/recovery process of the present invention is conducted in an atmosphere with an oxygen concentration of about 1000 ppm or lower. In a separation/extraction/recovery atmosphere with an oxygen concentration over about 1000 ppm, the phosphines and the phosphites are oxidized to form oxides, thereby reducing the catalyst activity when reused. This phenomenon is known in the art. In addition, the inventors have found that the transfer of rhodium into the aqueous extraction solvent is largely affected by the coexistence of oxygen. Namely, when the separation/extraction/recovery is carried out in the presence of oxygen, the transfer of rhodium into the aqueous extraction solvent becomes non-negligible to make the recycling of the catalyst impossible. Without being bound by theory, the reason for this is presumed that the produced dialdehyde is oxidized to carboxylic acid which in turn forms a rhodium carboxylate easily transferring into the aqueous extraction solvent, in consideration of the fact that the transferring amount of the organophosphorus compound into the aqueous extraction solvent does not change during the separation/extraction/recovery in the presence of oxygen.

The transferring amount of rhodium into the aqueous extraction solvent is reduced by regulating the oxygen concentration in the separation/extraction/recovery atmosphere to about 1000 ppm or lower, preferably about 100 ppm or lower. Atmosphere with an oxygen concentration of about 1000 ppm or lower may be created practically by replacing the separation/extraction/recovery atmosphere with carbon monoxide and hydrogen used in the hydroformylation or inert gas such as nitrogen, helium and argon. Since the aqueous extraction solvent for use in separation/extraction/recovery contains oxygen, the deaeration prior to its use to reduce the oxygen concentration is effective. The deaeration may be conducted by distillation under reduced pressure or blowing of nitrogen, carbon monoxide or hydrogen gas into the aqueous extraction solvent, thereby reducing the dissolved oxygen concentration. It is preferred to subject the hydrocarbon compound to similar treatment.

In some embodiments, the separation/extraction/recovery process of the present invention is conducted at an oxygen concentration of about 0 ppm-about 200 ppm. In some embodiments, the separation/extraction/recovery process of the present invention is conducted at an oxygen concentration of about 0 ppm-about 100 ppm.

Without being bound by theory, the partition of the hydroformylation catalyst between the non-aqueous hydroformylation solvent layer (e.g., nonpolar phase) and the aqueous extraction solvent layer (e.g., polar phase) is an equilibrium process.

In some embodiments, the separation/extraction/recovery process of the present invention does not produce an acetal compound. In some embodiments, the separation/extraction/recovery process of the present invention may produce a trace amount of an acetal compound. In some embodiments, the weight ratio of the high-boiling point aldehyde compound to the acetal compound is about 1:0.0001 to about 1:0.05. Thus, it is not necessary to add other substances (such as amine, tertiary amine, or inorganic base compound) for reducing the amount of the acetal compound. However, the separation/extraction/recovery process of the present invention does not exclude embodiments that include adding an amine, tertiary amine, or inorganic base compound. In some embodiments, the aqueous extraction solvent does not comprise a tertiary amine. In some embodiments, the aqueous extraction solvent further comprises a tertiary amine.

In some embodiments, a metal salt is added to the separation/extraction/recovery process to make the amount of the hydroformylation catalyst and/or hydroformylation catalyst component and/or ligand and/or active material transferred into the aqueous extraction solvent layer (i.e., polar phase) as little as possible. In some embodiments, a salting-out agent may be added to facilitate the phase separation in the biphasic mixture, without causing any disadvantage. In some embodiments, the aqueous extraction solvent comprises at least one metal salt. In some embodiments, the aqueous extraction solvent comprises at least one salting-out agent. In some embodiments, the aqueous extraction solvent does not comprise a metal salt. In some embodiments, the aqueous extraction solvent does not comprise a salting-out agent.

In some embodiments, the separation/extraction/recovery process of the present invention and the hydroformylation reaction can be conducted in the same or different reactors/vessels/extractors as are known to one of skill in the art. In some embodiments of the present invention, the hydroformylation reaction is conducted in a first reactor/vessel/extractor, and the non-aqueous hydroformylation product solution is transferred to a second reactor/vessel/extractor for the separation/extraction/recovery process.

In some embodiments, the separation/extraction/recovery process of the present invention may be conducted in the same reactor as used for the hydroformylation reaction, or in a separation/extraction/recovery vessel after introducing the non-aqueous hydroformylation product solution from the reactor into the separation/extraction/recovery vessel. When the separation/extraction/recovery process is conducted in the same reactor as used for the hydroformylation reaction, the remaining non-aqueous hydroformylation product solution can be reused in the next hydroformylation reaction while retaining the hydroformylation catalyst in the non-aqueous hydroformylation solvent layer. When the separation/extraction/recovery process is conducted in a separation/extraction/recovery vessel, the non-aqueous hydroformylation solvent layer is returned to the hydroformylation reactor for reuse. The separation/extraction/recovery process of the present invention may be conducted in either batch or continuous process.

The reactors/vessels/extractors for use in the present invention are not particularly limited. For example, static, mixer-settlers, rotary-agitated, reciprocating-plate, pulsed, centrifugal, baffle tray, sieve plate, packed, spray, baffle, packed column, rotating disk contactor, kuhni rotating-impeller column, karr reciprocating-plate column, scheibel rotating-impeller column and grasser raining-bucket contactor reactors/vessels/extractors can be used.

Furthermore, in some embodiments, the separation/extraction/recovery process of the present invention provides a separation/extraction/recovery efficiency of at least about 85%. In some embodiments, the separation/extraction/recovery process of the present invention provides a separation/extraction/recovery efficiency of at least about 90%. In some embodiments, the separation/extraction/recovery process of the present invention provides a separation/extraction/recovery efficiency of at least about 95%. In some embodiments, the separation/extraction/recovery efficiency is directed to the separation/extraction/recovery of the high-boiling point aldehyde compound.

In some embodiments, the aqueous extraction solvent has an extraction efficiency of at least about 85%. In some embodiments, the aqueous extraction solvent has an extraction efficiency of at least about 90%. In some embodiments, the aqueous extraction solvent has an extraction efficiency of at least about 95%. In some embodiments, the extraction efficiency of the aqueous extraction solvent is directed to the extraction of the high-boiling point aldehyde compound.

In some embodiments, the high-boiling point aldehyde compound has a partition coefficient (Kp) greater than 13.5. In some embodiments, the high-boiling point aldehyde compound has a partition coefficient (Kp) greater than 14.0. In some embodiments, the dialdehyde compound has a partition coefficient (Kp) greater than 14.0.

Primary Alcohols

In various embodiments, the primary alcohol is selected from a $C_1$-$C_3$ primary alcohol. In some embodiments, the primary alcohol is selected from methanol, ethanol, and n-propanol. In some embodiments, the primary alcohol is selected from methanol and ethanol.

Polyalcohols

In various embodiments, the polyalcohol is selected from a branched polyalcohol, acyclic polyalcohol, and cyclic polyalcohol. In various embodiments, the polyalcohol is selected from the group consisting of a branched polyalcohol, monocyclic polyalcohol, and polycyclic polyalcohol. In some embodiments, the polyalcohol is a $C_4$-$C_{20}$ polyalcohol. In some embodiments, the polyalcohol is selected from $C_4$-$C_{20}$ branched polyalcohol, $C_4$-$C_{20}$ acyclic polyalcohol, and $C_4$-$C_{20}$ cyclic polyalcohol. In some embodiments, the polyalcohol is selected from $C_4$-$C_{20}$ branched polyalcohol, $C_4$-$C_{20}$ monocyclic polyalcohol, and $C_4$-$C_{20}$ polycyclic polyalcohol.

In some embodiments, the polyalcohol is a $C_4$-$C_{20}$ polyalcohol, $C_4$-$C_{19}$ polyalcohol, $C_4$-$C_{18}$ polyalcohol, $C_4$-$C_{17}$ polyalcohol, $C_4$-$C_{16}$ polyalcohol, $C_4$-$C_{15}$ polyalcohol, $C_4$-$C_{14}$ polyalcohol, $C_4$-$C_{13}$ polyalcohol, $C_4$-$C_{12}$ polyalcohol, $C_4$-$C_{11}$ polyalcohol, $C_4$-$C_{10}$ polyalcohol, $C_4$-$C_9$ polyalcohol, $C_4$-$C_8$ polyalcohol, $C_4$-$C_7$ polyalcohol, $C_4$-$C_6$ polyalcohol, or $C_4$-$C_5$ polyalcohol.

In some embodiments, the polyalcohol is a $C_4$-$C_{20}$ polyalcohol, $C_5$-$C_{20}$ polyalcohol, $C_6$-$C_{20}$ polyalcohol, $C_7$-$C_{20}$ polyalcohol, $C_8$-$C_{20}$ polyalcohol, $C_9$-$C_{20}$ polyalcohol, $C_{10}$-$C_{20}$ polyalcohol, $C_{11}$-$C_{20}$ polyalcohol, $C_{12}$-$C_{20}$ polyalcohol, $C_{13}$-$C_{20}$ polyalcohol, $C_{14}$-$C_{20}$ polyalcohol, $C_{15}$-$C_{20}$ polyalcohol, $C_{16}$-$C_{20}$ polyalcohol, $C_{17}$-$C_{20}$ polyalcohol, $C_{18}$-$C_{20}$ polyalcohol, or $C_{19}$-$C_{20}$ polyalcohol.

In some embodiments, the polyalcohol is a $C_4$-$C_{20}$ branched polyalcohol, $C_4$-$C_{19}$ branched polyalcohol, $C_4$-$C_{18}$ branched polyalcohol, $C_4$-$C_{17}$ branched polyalcohol, $C_4$-$C_{16}$ branched polyalcohol, $C_4$-$C_{15}$ branched polyalcohol, $C_4$-$C_{14}$ branched polyalcohol, $C_4$-$C_{13}$ branched polyalcohol, $C_4$-$C_{12}$ branched polyalcohol, $C_4$-$C_{11}$ branched polyalcohol, $C_4$-$C_{10}$ branched polyalcohol, $C_4$-$C_9$ branched polyalcohol, $C_4$-$C_8$ branched polyalcohol, $C_4$-$C_7$ branched polyalcohol, $C_4$-$C_6$ branched polyalcohol, or $C_4$-$C_5$ branched polyalcohol.

In some embodiments, the polyalcohol is a $C_4$-$C_{20}$ branched polyalcohol, $C_5$-$C_{20}$ branched polyalcohol, $C_6$-$C_{20}$ branched polyalcohol, $C_7$-$C_{20}$ branched polyalcohol, $C_8$-$C_{20}$ branched polyalcohol, $C_9$-$C_{20}$ branched polyalcohol, $C_{10}$-$C_{20}$ branched polyalcohol, $C_{11}$-$C_{20}$ branched polyalcohol, $C_{12}$-$C_{20}$ branched polyalcohol, $C_{13}$-$C_{20}$ branched polyalcohol, $C_{14}$-$C_{20}$ branched polyalcohol, $C_{15}$-$C_{20}$ branched polyalcohol, $C_{16}$-$C_{20}$ branched polyalcohol, $C_{17}$-$C_{20}$ branched polyalcohol, $C_{18}$-$C_{20}$ branched polyalcohol, or $C_{19}$-$C_{20}$ branched polyalcohol.

In some embodiments, the polyalcohol is a $C_4$-$C_{20}$ acyclic polyalcohol, $C_4$-$C_{19}$ acyclic polyalcohol, $C_4$-$C_{18}$ acyclic polyalcohol, $C_4$-$C_{17}$ acyclic polyalcohol, $C_4$-$C_{16}$ acyclic polyalcohol, $C_4$-$C_{15}$ acyclic polyalcohol, $C_4$-$C_{14}$ acyclic polyalcohol, $C_4$-$C_{13}$ acyclic polyalcohol, $C_4$-$C_{12}$ acyclic polyalcohol, $C_4$-$C_{11}$ acyclic polyalcohol, $C_4$-$C_{10}$ acyclic polyalcohol, $C_4$-$C_9$ acyclic polyalcohol, $C_4$-$C_8$ acyclic polyalcohol, $C_4$-$C_7$ acyclic polyalcohol, $C_4$-$C_6$ acyclic polyalcohol, or $C_4$-$C_5$ acyclic polyalcohol.

In some embodiments, the polyalcohol is a $C_4$-$C_{20}$ acyclic polyalcohol, $C_5$-$C_{20}$ acyclic polyalcohol, $C_6$-$C_{20}$ acyclic polyalcohol, $C_7$-$C_{20}$ acyclic polyalcohol, $C_8$-$C_{20}$ acyclic polyalcohol, $C_9$-$C_{20}$ acyclic polyalcohol, $C_{10}$-$C_{20}$ acyclic polyalcohol, $C_{11}$-$C_{20}$ acyclic polyalcohol, $C_{12}$-$C_{20}$ acyclic polyalcohol, $C_{13}$-$C_{20}$ acyclic polyalcohol, $C_{14}$-$C_{20}$ acyclic polyalcohol, $C_{15}$-$C_{20}$ acyclic polyalcohol, $C_{16}$-$C_{20}$ acyclic polyalcohol, $C_{17}$-$C_{20}$ acyclic polyalcohol, $C_{18}$-$C_{20}$ acyclic polyalcohol, or $C_{19}$-$C_{20}$ acyclic polyalcohol.

In some embodiments, the polyalcohol is a $C_4$-$C_{20}$ cyclic polyalcohol, $C_4$-$C_{19}$ cyclic polyalcohol, $C_4$-$C_{18}$ cyclic polyalcohol, $C_4$-$C_{17}$ cyclic polyalcohol, $C_4$-$C_{16}$ cyclic polyalcohol, $C_4$-$C_{15}$ cyclic polyalcohol, $C_4$-$C_{14}$ cyclic polyalcohol, $C_4$-$C_{13}$ cyclic polyalcohol, $C_4$-$C_{12}$ cyclic polyalcohol, $C_4$-$C_{11}$ cyclic polyalcohol, $C_4$-$C_{10}$ cyclic polyalcohol, $C_4$-$C_9$ cyclic polyalcohol, $C_4$-$C_8$ cyclic polyalcohol, $C_4$-$C_7$ cyclic polyalcohol, $C_4$-$C_6$ cyclic polyalcohol, or $C_4$-$C_5$ cyclic polyalcohol.

In some embodiments, the polyalcohol is a $C_4$-$C_{20}$ cyclic polyalcohol, $C_5$-$C_{20}$ cyclic polyalcohol, $C_6$-$C_{20}$ cyclic polyalcohol, $C_7$-$C_{20}$ cyclic polyalcohol, $C_8$-$C_{20}$ cyclic polyalcohol, $C_9$-$C_{20}$ cyclic polyalcohol, $C_{10}$-$C_{20}$ cyclic polyalcohol, $C_{11}$-$C_{20}$ cyclic polyalcohol, $C_{12}$-$C_{20}$ cyclic polyalcohol, $C_{13}$-$C_{20}$ cyclic polyalcohol, $C_{14}$-$C_{20}$ cyclic polyalcohol, $C_{15}$-$C_{20}$ cyclic polyalcohol, $C_{16}$-$C_{20}$ cyclic polyalcohol, $C_{17}$-$C_{20}$ cyclic polyalcohol, $C_{18}$-$C_{20}$ cyclic polyalcohol, or $C_{19}$-$C_{20}$ cyclic polyalcohol.

In some embodiments, the polyalcohol is a $C_4$-$C_{20}$ monocyclic polyalcohol, $C_4$-$C_{19}$ monocyclic polyalcohol, $C_4$-$C_{18}$ monocyclic polyalcohol, $C_4$-$C_{17}$ monocyclic polyalcohol, $C_4$-$C_{16}$ monocyclic polyalcohol, $C_4$-$C_{15}$ monocyclic polyalcohol, $C_4$-$C_{14}$ monocyclic polyalcohol, $C_4$-$C_{13}$ monocyclic polyalcohol, $C_4$-$C_{12}$ monocyclic polyalcohol, $C_4$-$C_{11}$ monocyclic polyalcohol, $C_4$-$C_{10}$ monocyclic polyalcohol, $C_4$-$C_9$ monocyclic polyalcohol, $C_4$-$C_8$ monocyclic polyalcohol, $C_4$-$C_7$ monocyclic polyalcohol, $C_4$-$C_6$ monocyclic polyalcohol, or $C_4$-$C_5$ monocyclic polyalcohol.

In some embodiments, the polyalcohol is a $C_4$-$C_{20}$ monocyclic polyalcohol, $C_5$-$C_{20}$ monocyclic polyalcohol, $C_6$-$C_{20}$ monocyclic polyalcohol, $C_7$-$C_{20}$ monocyclic polyalcohol, $C_8$-$C_{20}$ monocyclic polyalcohol, $C_9$-$C_{20}$ monocyclic polyalcohol, $C_{10}$-$C_{20}$ monocyclic polyalcohol, $C_{11}$-$C_{20}$ monocyclic polyalcohol, $C_{12}$-$C_{20}$ monocyclic polyalcohol, $C_{13}$-$C_{20}$ monocyclic polyalcohol, $C_{14}$-$C_{20}$ monocyclic polyalcohol, $C_{15}$-$C_{20}$ monocyclic polyalcohol, $C_{16}$-$C_{20}$ monocyclic polyalcohol, $C_{17}$-$C_{20}$ monocyclic polyalcohol, $C_{18}$-$C_{20}$ monocyclic polyalcohol, or $C_{19}$-$C_{20}$ monocyclic polyalcohol.

In some embodiments, the polyalcohol is a $C_4$-$C_{20}$ polycyclic polyalcohol, $C_4$-$C_{19}$ polycyclic polyalcohol, $C_4$-$C_{18}$ polycyclic polyalcohol $C_4$-$C_{17}$ polycyclic polyalcohol, $C_4$-$C_{16}$ polycyclic polyalcohol, $C_4$-$C_{15}$ polycyclic polyalcohol, $C_4$-$C_{14}$ polycyclic polyalcohol, $C_4$-$C_{13}$ polycyclic polyalcohol, $C_4$-$C_{12}$ polycyclic polyalcohol, $C_4$-$C_{11}$ polycyclic polyalcohol, $C_4$-$C_{10}$ polycyclic polyalcohol, $C_4$-$C_9$ polycyclic polyalcohol, $C_4$-$C_8$ polycyclic polyalcohol, $C_4$-$C_7$ polycyclic polyalcohol, $C_4$-$C_6$ polycyclic polyalcohol, or $C_4$-$C_5$ polycyclic polyalcohol.

In some embodiments, the polyalcohol is a $C_4$-$C_{20}$ polycyclic polyalcohol, $C_5$-$C_{20}$ polycyclic polyalcohol, $C_6$-$C_{20}$ polycyclic polyalcohol, $C_7$-$C_{20}$ polycyclic polyalcohol, $C_8$-$C_{20}$ polycyclic polyalcohol, $C_9$-$C_{20}$ polycyclic polyalcohol, $C_{10}$-$C_{20}$ polycyclic polyalcohol, $C_{11}$-$C_{20}$ polycyclic polyalcohol, $C_{12}$-$C_{20}$ polycyclic polyalcohol, $C_{13}$-$C_{20}$ polycyclic polyalcohol, $C_{14}$-$C_{20}$ polycyclic polyalcohol, $C_{15}$-$C_{20}$ polycyclic polyalcohol, $C_{16}$-$C_{20}$ polycyclic polyalcohol, $C_{17}$-$C_{20}$ polycyclic polyalcohol, $C_{18}$-$C_{20}$ polycyclic polyalcohol, or $C_{19}$-$C_{20}$ polycyclic polyalcohol.

In some embodiments, the polyalcohol is a compound of Formula (I):

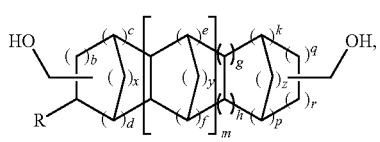

(I)

wherein, R is selected from H and $CH_3$; x is an integer selected from 0 and 1; y is an integer selected from 0 and 1; z is an integer selected from 0 and 1; b is an integer selected from 0 and 1; c is an integer selected from 0 and 1; d is an integer selected from 0 and 1; e is an integer selected from 0 and 1; f is an integer selected from 0 and 1; g is an integer selected from 0 and 1; h is an integer selected from 0 and 1; k is an integer selected from 0 and 1; p is an integer selected from 0 and 1; q is an integer selected from 0 and 1; r is an integer selected from 0 and 1; and m is an integer selected from 0 and 1.

In some embodiments, the polyalcohol is selected from the group consisting of 2-methyl-1,3-propanediol; a compound of Formula (II):

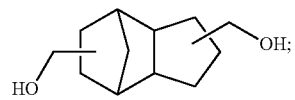

(II)

a compound of Formula (III):

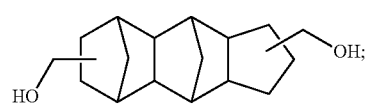

(III)

a compound of Formula (IV):

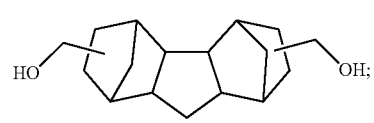

(IV)

and a compound of Formula (V):

(V)

In some embodiments, the polyalcohol is selected from the group consisting of 2-methyl-1,3-propanediol; 1,1-cyclohexanedimethanol; 1,2-cyclohexanedimethanol; 1,3-cyclohexanedimethanol; 1,4-cyclohexanedimethanol; 3,8-bis(hydroxymethyl)tricyclo[5.2.1.0$^{2-6}$]decane; 3,9-bis(hydroxymethyl)tricyclo[5.2.1.0$^{2-6}$]decane; 4,8-bis(hydroxymethyl)tricyclo[5.2.1.0$^{2-6}$]decane; 4,9-bis(hydroxymethyl)tricyclo[5.2.1.0$^{2-6}$]decane; 5,8-bis(hydroxymethyl)tricyclo[5.2.1.0$^{2-6}$]decane; 5,9-bis(hydroxymethyl)tricyclo[5.2.1.0$^{2-6}$]decane; 4,10-bis(hydroxymethyl)pentacyclo[6.5.1.1$^{3-6}$.0$^{2-7}$.0$^{9-13}$]pentadecane; 4,11-bis(hydroxymethyl)pentacyclo[6.5.1.1$^{3-6}$.0$^{2-7}$.0$^{9-13}$]pentadecane; 4,12-bis(hydroxymethyl)pentacyclo[6.5.1.1$^{3-6}$.0$^{2-7}$.0$^{9-13}$]pentadecane; 5,10-bis(hydroxymethyl)pentacyclo[6.5.1.1$^{3-6}$.0$^{2-7}$.0$^{9-13}$]pentadecane; 5,11-bis(hydroxymethyl)pentacyclo[6.5.1.1$^{3-6}$.0$^{2-7}$.0$^{9-13}$]pentadecane; 5,12-bis(hydroxymethyl)pentacyclo[6.5.1.1$^{3-6}$.0$^{2-7}$.0$^{9-13}$]pentadecane; 5,12-bis(hydroxymethyl)pentacyclo[9.2.1.1$^{4-7}$.0$^{2-10}$.0$^{3-8}$]pentadecane; 5,13-bis(hydroxymethyl)pentacyclo[9.2.1.1$^{4-7}$.0$^{2-10}$.0$^{3-8}$]pentadecane; 6,12-bis(hydroxymethyl)pentacyclo[9.2.1.1$^{4-7}$.0$^{2-10}$.0$^{3-8}$]pentadecane; and 6,13-bis(hydroxymethyl)pentacyclo[9.2.1.1$^{4-7}$.0$^{2-10}$.0$^{3-8}$]pentadecane.

In some embodiments, the polyalcohol is 2-methyl-1,3-propanediol. In some embodiments, the polyalcohol is a compound of Formula (II):

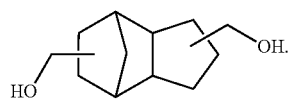

Biphasic Mixture

In some embodiments, the biphasic mixture comprises the non-aqueous hydroformylation solvent layer; and the aqueous extraction solvent layer. In some embodiments, the non-aqueous hydroformylation solvent layer is a nonpolar phase. In some embodiments, the aqueous extraction solvent layer is a polar phase. In some embodiments, the non-aqueous hydroformylation solvent layer is a light phase. In some embodiments, the aqueous extraction solvent layer is a heavy phase.

Aqueous Extraction Solvent Layer

In various embodiments, the aqueous extraction solvent layer comprises at least one high-boiling point aldehyde compound, and an aqueous extraction solvent. In some embodiments, the aqueous extraction solvent layer further comprises at least one acetal compound.

In various embodiments, the aqueous extraction solvent layer comprises an aldehyde product composition, and an aqueous extraction solvent. In some embodiments, the aldehyde product composition comprises at least one high-boiling point aldehyde compound. In some embodiments, the aldehyde product composition further comprises at least one acetal compound.

In some embodiments, the aqueous extraction solvent layer comprises a second portion of the hydroformylation catalyst. In some embodiments, the hydroformylation catalyst comprises a hydroformylation catalyst component, and a ligand, wherein the hydroformylation catalyst component comprises an active material. In some embodiments, the content (or amount) of the active material in the aqueous extraction solvent layer is less than about 2 ppm.

In some embodiments, the content (or the amount) of the active material in the aqueous extraction solvent layer is less than about 2 ppm, less than about 500 ppb, less than about 400 ppb, or less than about 350 ppb. In some embodiments, the content (or the amount) of the active material in the aqueous extraction solvent layer is about 2000 ppb to about 100 ppb, about 2000 ppb to about 200 ppb, about 2000 to about 300 ppb, about 2000 to about 400 ppb, about 2000 to about 500 ppb, about 2000 ppb to about 600 ppb, about 2000 ppb to about 700 ppb, about 2000 ppb to about 800 ppb, about 2000 ppb to about 900 ppb, about 2000 ppb to about 1000 ppb, about 2000 ppb to about 1100 ppb, about 2000 ppb to about 1200 ppb, about 2000 ppb to about 1300 ppb, about 2000 ppb to about 1400 ppb, about 2000 ppb to about 1500 ppb, about 2000 ppb to about 1600 ppb, about 2000 ppb to about 1700 ppb, about 2000 ppb to about 1800 ppb, or about 2000 ppb to about 1900 ppb. In some embodiments, the content (or the amount) of the active material in the aqueous extraction solvent layer is about 2000 ppb to about 100 ppb, about 1900 ppb to about 100 ppb, about 1800 ppb to about 100 ppb, about 1700 ppb to about 100 ppb, about 1600 ppb to about 100 ppb, about 1500 ppb to about 100 ppb, about 1400 ppb to about 100 ppb, about 1300 ppb to about 100 ppb, about 1200 ppb to about 100 ppb, about 1100 ppb to about 100 ppb, about 1000 ppb to about 100 ppb, about 900 ppb to about 100 ppb, about 800 ppb to about 100 ppb, about 700 ppb to about 100 ppb, about 600 ppb to about 100 ppb, about 500 ppb to about 100 ppb, about 400 ppb to about 100 ppb, about 300 ppb to about 100 ppb, or about 200 ppb to about 100 ppb.

In some embodiments, the aqueous extraction solvent layer has a pH value of less than about 7. In some embodiments, the aqueous extraction solvent layer has a pH value of about 7 to about 1, about 7 to about 2, about 7 to about 3, about 7 to about 4, about 7 to about 5, or about 7 to about 6. In some embodiments, the aqueous extraction solvent layer has a pH value of about 7 to about 1, about 6 to about 1, about 5 to about 1, about 4 to about 1, about 3 to about 1, or about 2 to about 1. In some embodiments, the aqueous extraction solvent layer has a pH value of about 5 to about 7. In some embodiments, the aqueous extraction solvent layer has a pH value of about 6.

In some embodiments, the aqueous extraction solvent layer has a viscosity of less than or equal to about 100 centipoise (cP) at about 25° C. In some embodiments, the aqueous extraction solvent layer has a viscosity of about 100 centipoise (cP) to about 50 centipoise (cP) at about 25° C., about 100 centipoise (cP) to about 55 centipoise (cP) at about 25° C., about 100 centipoise (cP) to about 60 centipoise (cP) at about 25° C., about 100 centipoise (cP) to about 65 centipoise (cP) at about 25° C., about 100 centipoise (cP) to about 70 centipoise (cP) at about 25° C., about 100 centipoise (cP) to about 75 centipoise (cP) at about 25° C., about 100 centipoise (cP) to about 80 centipoise (cP) at about 25° C., about 100 centipoise (cP) to about 85 centipoise (cP) at about 25° C., about 100 centipoise (cP) to about 90 centipoise (cP) at about 25° C., or about 100 centipoise (cP) to about 95 centipoise (cP) at about 25° C.

In some embodiments, the aqueous extraction solvent layer is a polar phase.

Aldehyde Product Composition

In various embodiments, the aldehyde product composition comprises at least one high-boiling point aldehyde compound. In some embodiments, the aldehyde product composition further comprises at least one acetal compound. In some embodiments, the aldehyde product composition comprises at least one high-boiling point aldehyde compound, and at least one acetal compound. In some embodiments, the aldehyde product composition further comprises at least one hemiacetal. In some embodiments, the aldehyde product composition further comprises at least one hemiacetal and at least one acetal compound. In some embodiments, the high-boiling point aldehyde compound has a boiling point of at least about 100° C. at atmospheric pressure.

In some embodiments, a weight ratio of the high-boiling point aldehyde compound to the acetal compound in the aldehyde product composition is about 1:0.0001 to about 1:0.05 (high-boiling point aldehyde compound:acetal compound); preferably about 1:0.0001 to about 1:0.04 (high-boiling point aldehyde compound:acetal compound); and more preferably about 1:0.001 to about 1:0.04 (high-boiling point aldehyde compound:acetal compound).

In various embodiments, the aldehyde product composition of the present invention may be processed according to any industrial process. Non-limiting examples of industrial processes include a process for preparing an alcohol or amino derivative; a process for preparing an alcohol; a hydrogenation process for preparing tricyclodecane dimethanol; and/or a hydrogenation process for preparing pentacyclopentadecane dimethanol.

High-Boiling Point Aldehyde Compound

In various embodiments, the high-boiling point aldehyde compound is a compound of Formula (VI):

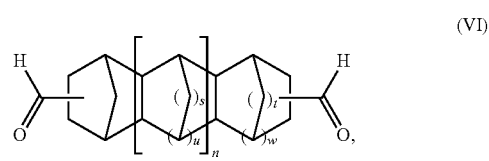

(VI)

wherein, s is an integer selected from 0 and 1; t is an integer selected from 0 and 1; u is an integer selected from 0 and 1; w is an integer selected from 0 and 1; and n is an integer selected from 0 and 1.

In some embodiments, the high-boiling point aldehyde compound is selected from the group consisting of a compound of Formula (VII):

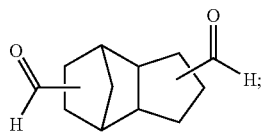
(VII)

a compound of Formula (VIII):

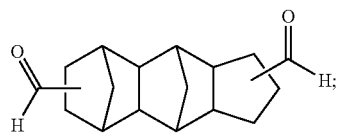
(VIII)

and a compound of Formula (IX):

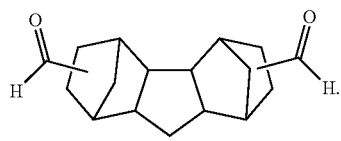
(IX)

In some embodiments, the high-boiling point aldehyde compound is a compound of Formula (VII):

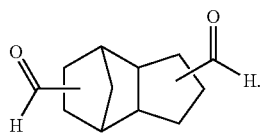

In some embodiments, the high-boiling point aldehyde compound is selected from tricyclodecane dialdehyde and pentacyclopentadecane dialdehyde.

In some embodiments, the high-boiling point aldehyde compound is selected from at least one of monoaldehyde compound and dialdehyde compound. In some embodiments, the high-boiling point aldehyde compound is selected from monoaldehyde compound and dialdehyde compound. In some embodiments, the high-boiling point aldehyde compound is a dialdehyde compound. In some embodiments, the high-boiling point aldehyde compound is a monoaldehyde compound. In some embodiments, the high-boiling point aldehyde compound is not a monoaldehyde compound.

In various embodiments, the high-boiling point aldehyde compound has a boiling point of at least about 100° C. at atmospheric pressure.

Acetal Compound

In various embodiments, the acetal compound is present in the aqueous extraction solvent layer at a content (or an amount) of about 0.01% to about 1.00% by weight as calculated herein. In some embodiments, the acetal compound is present in the aqueous extraction solvent layer at a content (or an amount) of about 0.01% to about 1.00%, about 0.01% to about 0.90%, about 0.01% to about 0.80%, about 0.01% to about 0.70%, about 0.01% to about 0.60%, about 0.01% to about 0.50%, about 0.01% to about 0.40%, about 0.01% to about 0.30%, about 0.01% to about 0.20%, about 0.01% to about 0.10%, or about 0.01% to about 0.05% by weight as calculated herein. In some embodiments, the acetal compound is present in the aqueous extraction solvent layer at a content (or an amount) of about 0.01% to about 1.00%, about 0.05% to about 1.00%, about 0.10% to about 1.00%, about 0.20% to about 1.00%, about 0.30% to about 1.00%, about 0.40% to about 1.00%, about 0.50% to about 1.00%, about 0.60% to about 1.00%, about 0.70% to about 1.00%, about 0.80% to about 1.00%, or about 0.90% to about 1.00% by weight as calculated herein.

In some embodiments, the acetal compound is present in the aqueous extraction solvent layer at a content (or an amount) of less than about 1.00% by weight as calculated herein. In some embodiments, the acetal compound is present in the aqueous extraction solvent layer at a content (or an amount) of less than about 0.70% by weight as calculated herein. In some embodiments, the acetal compound is present in the aqueous extraction solvent layer at a content (or an amount) of less than about 0.40% by weight as calculated herein. In some embodiments, the acetal compound is present in the aqueous extraction solvent layer at a content (or an amount) of less than about 0.10% by weight as calculated herein.

In some embodiments, the acetal compound is selected from at least one of monoacetal compound and diacetal compound. In some embodiments, the acetal compound is selected from monoacetal compound and diacetal compound. In some embodiments, the acetal compound is a monoacetal compound. In some embodiments, the acetal compound is a diacetal compound.

Hydroformylation Catalysts, Hydroformylation Catalyst Components, Active Materials, and Ligands The hydroformylation catalyst is not particularly limited. In some embodiments, the hydroformylation catalyst comprises at least one hydroformylation catalyst component, and at least one ligand. In some embodiments, the hydroformylation catalyst component comprises at least one active material.

In some embodiments, the hydroformylation catalyst component is a rhodium compound. Such rhodium compounds are not particularly limited as far as they form a complex with a ligand (e.g., an organophosphorus compound) and show activity of hydroformylation in the presence of hydrogen and carbon monoxide. Examples of such rhodium compounds include $Rh(acac)(CO)_2$, $Rh_2O_3$, $Rh_4(CO)_{12}$, $Rh_6(CO)_{16}$ and $Rh(NO_3)_3$. In some embodiments, without being limited by theory, the precursor of such rhodium compounds can also be used, for example, but not limited to $Rh(acac)(CO)_xL_y$, wherein x and y are each independently an integer and x+y=2, and L is a phosphorus complex. In some embodiments, the hydroformylation catalyst component (e.g., rhodium compound) may be added to a starting mixture together with a ligand (e.g., an organophosphorus compound) to create a catalytically active rhodium hydride-carbonyl-phosphorus complex (i.e., hydroformylation catalyst) in a reaction vessel. Alternatively, the rhodium hydride-carbonyl-phosphorus complex (i.e., hydroformylation catalyst) may be prepared in advance and added to a reaction vessel. In one embodiment of the present invention, Rh(acac)(CO)$_2$ as a hydroformylation catalyst component is reacted with a ligand (e.g., an organophosphorus compound) in the presence of a solvent, and then the resultant product is introduced into a reaction vessel together with an excess of free organophosphorus compound, thereby forming catalytically active rhodium-organophosphorus complex (i.e., a hydroformylation catalyst). In some embodiments, it is sufficient that the active rhodium-organophosphorus catalyst (i.e. hydroformylation catalyst) is present in the reaction system during the hydroformylation in the presence of hydrogen and carbon monoxide.

In some embodiments, the hydroformylation catalyst comprises rhodium. In some embodiments, the hydroformylation catalyst component comprises rhodium. In some embodiments, the hydroformylation catalyst component comprises an active material, wherein the active material is rhodium. Non-limiting examples of hydroformylation catalyst components include Rh(acac)(CO)$_2$, Rh$_2$O$_3$, Rh$_4$(CO)$_{12}$, Rh$_6$(CO)$_{16}$, or Rh(NO$_3$)$_3$.

In some embodiments, the hydroformylation catalyst comprises cobalt. In some embodiments, the hydroformylation catalyst component comprises cobalt. In some embodiments, the hydroformylation catalyst component comprises an active material, wherein the active material is cobalt. Non-limiting examples of hydroformylation catalyst components include HCo(CO)$_4$, HCo(CO)$_3$(PR$_3$), or Co$_2$(CO)$_8$.

The amount of hydroformylation catalyst contained in the non-aqueous hydroformylation product solution is not particularly limited. In some embodiments, the amount of hydroformylation catalyst contained in the non-aqueous hydroformylation product solution is about 0.005 wt % to about 0.05 wt %.

In some embodiments, the ligand is a hydroformylation catalyst ligand. In some embodiments, the ligand is an organophosphorus compound.

The ligands for use with the hydroformylation catalyst components are not particularly limited. In some embodiments, the ligand comprises at least one selected from the group consisting of a phosphite, phosphine, and combinations thereof.

In some embodiments, the ligand comprises a phosphite. In some embodiments, the ligand is a phosphite. Non-limiting examples of phosphites suitable for use in the present invention include phosphites which are represented by the formula: P(—OR$^1$)(—OR$^2$)(—OR$^3$), wherein R$^1$, R$^2$, and R$^3$ are independently aryl or alkyl which may be substituted, and have an electronic parameter (v) of 2080 to 2090 cm$^{-1}$ and a steric parameter (θ) of 135 to 190 degrees. The electronic parameter (v) and the steric parameter (θ) are defined in C. A. Tolman, Chemical Reviews, vol. 77, p. 313, 1977. The electronic parameter (v) is used to rank electronic effect of phosphorus compounds in the formation of metal complex and is calculated based on the carbonyl stretching frequencies of Ni-carbonyl complex. The steric parameter (θ) is used to evaluate the steric effect of phosphorus compounds and is calculated from cone angles of molecular models. Non-limiting examples of R$^1$, R$^2$ and R$^3$ are aryl such as phenyl and naphthyl which may be substituted by methyl, ethyl, isopropyl, n-butyl, t-butyl or methoxy; aliphatic alkyl such as methyl, ethyl, isopropyl, n-butyl and t-butyl; and alicyclic alkyl such as cyclopentyl and cyclohexyl which may be substituted by lower alkyl such as methyl, ethyl, isopropyl, n-butyl and t-butyl. Non-limiting examples of phosphites include triphenylphosphite, tris(2-t-butylphenyl)phosphite, tris(3-methyl-6-t-butylphenyl) phosphite, tris(3-methoxy-6-t-butylphenyl)phosphite, tris(2, 4-di-t-butylphenyl)phosphite and di(2-t-butylphenyl)-t-butylphosphite. These phosphites may be used alone or in combination of two or more. In addition to the above triorganophosphites, also usable are bisphosphites described in Japanese Patent Application Laid-Open Nos. 61-501268, 8-165266, 8-337550, 10-45776 and 10-130190. Further, phosphite ligands having asymmetric carbon may be used.

In some embodiments, the ligand comprises a phosphine. In some embodiments, the ligand is a phosphine. Phosphines, particularly hindered alkylphosphines are known to be effective for hydroformylating internal olefins such as dicyclopentadiene and tricyclopentadiene (U.S. Pat. Nos. 3,168,553, 2,239,566, and 3,511,880). Non-limiting examples of phosphines suitable for use in the present invention include a tertiary phosphine substituted by alkyl, arylalkyl, cycloalkyl such as cyclohexyl and aryl such as phenyl which may be substituted by one or more alkyl. Non-limiting examples of tertiary phosphine includes trialkylphosphines such as tri-n-butylphosphine, tricyclohexylphosphine and dicyclohexyl-n-octylphosphine; triarylphosphines such as triphenylphosphine, tri-o-tolylphosphine and trinapthylphosphine; arylalkylphosphines such as dicyclohexylphenylphosphine, cyclohexyldiphenylphosphine and diphenyl-n-hexylphosphine. Also useable are bidentate chelate phosphine such as α,α'-bis(diphenylphosphino)-o-xylene, 2,2'-bis(diphenylphosphinomethyl)-1,1'-biphenyl, trans-1,2-bis(diphenylphosphinomethyl)-1,1'-biphenyl, trans-1,2-bis(diphenylphosphinomethyl)cyclobutene, 1,4-bis(diphenylphosphino)butane and 1,2-bis(diphenylphosphino)ethane; and 2,2'-bis(diphenylphosphino)-1,1'-binaphthyl (BINAP) and its derivatives widely used as asymmetric ligands. Non-limiting examples of tricycloalkylphosphines include those having a steric parameter (0) of 135 to 1900. Non-limiting examples of tricycloalkylphosphines include tricyclopropylphosphine, tricyclobutylphosphine, tricyclopentylphosphine, tricyclohexylphosphine, tricycloheptylphosphine and tricyclooctylphosphine. These phosphines may be used alone or in combination of two or more.

In some embodiments, the ligand is tris-(2,4-di-t-butylphenyl)phosphite.

The amount of ligand contained in the non-aqueous hydroformylation product solution is not particularly limited. In some embodiments, the amount of ligand contained in the non-aqueous hydroformylation product solution is about 0.2 wt % to about 2 wt %.

Without being bound by theory, the partition of the ligand between the non-aqueous hydroformylation solvent layer (e.g., nonpolar phase) and the aqueous extraction solvent layer (e.g., polar phase) is an equilibrium process. In some embodiments, the ligand has a high solubility to the non-aqueous hydroformylation solvent and low solubility to the aqueous extraction solvent. For example, by the use of a ligand having a solubility to the non-aqueous hydroformylation solvent 10 times higher than that to the aqueous extraction solvent, the partition coefficient of the ligand to the non-aqueous hydroformylation solvent becomes 10 or larger, thereby sufficiently preventing the ligand from transferring to the aqueous extraction solvent layer. For example, by the use of a ligand having a solubility to the non-aqueous hydroformylation solvent 100 times higher than that to the aqueous extraction solvent, the partition coefficient of the ligand to the non-aqueous hydroformylation solvent becomes 100 or larger, thereby easily reducing the transfer of the ligand into the aqueous extraction solvent layer to 1% or lower.

The active material of the present application can be purchased or prepared by any known process. In some embodiments, the active material is selected from at least one of rhodium and cobalt. In some embodiments, the active material is selected from rhodium and cobalt. In some embodiments, the active material comprises rhodium. In some embodiments, the active material is rhodium. In some embodiments, the active material comprises cobalt. In some embodiments, the active material is cobalt.

In some embodiments of the present invention, the hydroformylation catalyst component and the ligand are mixed together to prepare the hydroformylation catalyst during the hydroformylation reaction. In some embodiments, the hydroformylation catalyst component and the ligand are mixed in advance and added to a reaction vessel. In some embodiments, the hydroformylation catalyst component can be mixed with the ligand during the hydroformylation reaction. In some embodiments, the hydroformylation catalyst component can be mixed with the ligand in advance and added to a reaction vessel. For example, $Rh(acac)(CO)_2$ as a hydroformylation catalyst component can be mixed and reacted with a ligand (e.g., tris-(2,4-di-t-butylphenyl)phosphite) in the presence of a solvent and then the resultant product (e.g., hydroformylation catalyst) is introduced into a reaction vessel.

Various modifications to the hydroformylation reaction are well known to one of skill in the art. During the hydroformylation reaction, when the pressure is lower than about 1.0 MPa, the hydroformylation reaction proceeds slowly. A pressure higher than about 15 MPa requires a high-pressure apparatus which increases the overall cost of the apparatus. In some embodiments, the hydroformylation reaction is carried out under a pressure of about 0.2 to about 3 $kg/cm^2G$. When the hydroformylation reaction temperature is lower than about 40° C., the hydroformylation proceeds slowly. When the hydroformylation reaction temperature is higher than about 160° C., side reactions associated with dicyclopentadiene, tricyclopentadiene and other hydroformylation products become significant, thereby reducing the reaction yield.

Catalytic Hydrogenation

The hydrogenation catalyst used for hydrogenating the aqueous extraction solvent layer and/or aldehyde product composition and/or high-boiling point aldehyde (e.g., tricyclodecane dialdehyde and/or pentacyclopentadecane dialdehyde) is not particularly limited and may be any known metal catalyst having ability of hydrogenation, for example, Group VIII metals of the Periodic Table such as nickel, cobalt, ruthenium, palladium, rhodium and platinum, copper chromite, copper-zinc, etc. These metal catalysts are used in element form, oxide form, supported form on inorganic carrier such as silica, alumina, diatomaceous earth and carbon, or metal complex form. Particularly preferred are Raney nickel, nickel/diatomaceous earth, copper chromite, ruthenium/carbon, ruthenium/alumina in view of high hydrogenation rate and easiness of recovery.

The hydrogenation may be conducted in batch manner where a catalyst slurry is charged into a stirring reactor and the catalyst is separated from the product solution after hydrogenation by sedimentation and filtration. Alternatively, a flowing liquid method may be employed, where a shaped catalyst is disposed in a tubular reactor and the product solution and hydrogen gas are permitted to flow over the catalyst. The amount of the hydrogenation catalyst to be used is not particularly limited and can be easily determined so as to produce a high-boiling point alcohol compound (e.g., tricyclodecane dimethanol and pentacyclopentadecane dimethanol) in industrially advantageous productivity.

The hydrogenation temperature is not particularly limited. In some embodiments, the hydrogenation temperature is about 40° C. to about 200° C., preferably about 70° C. to about 150° C., and the hydrogenation pressure is about 10 MPa or lower.

The crude reaction solution containing the high-boiling point alcohol compound (e.g., tricyclodecane dimethanol, pentacyclopentadecane dimethanol) and the solvent is easily recovered and purified by common methods. For example, tricyclodecane dimethanol and pentacyclopentadecane dimethanol are separated and purified by thin film evaporation or distillation of crude products after distilling off the solvent. In some embodiments, the high-boiling point alcohol compound is selected from the group consisting of tricyclodecane dimethanol, pentacyclopentadecane dimethanol, and combinations thereof.

In some embodiments, the high-boiling point alcohol compound is a dialcohol compound. In some embodiments, the high-boiling point alcohol compound is a dialcohol compound obtained by hydrogenation of the corresponding high-boiling point aldehyde compound, wherein the high-boiling point aldehyde compound is a dialdehyde compound. In various embodiments, the high-boiling point alcohol compound has a boiling point of at least about 100° C. at atmospheric pressure.

In some embodiments, the process further comprises subjecting the aqueous extraction solvent layer to catalytic hydrogenation, thereby converting the high-boiling point aldehyde compound into corresponding high-boiling point alcohol compound.

In some embodiments, the process further comprises subjecting the aldehyde product composition to catalytic hydrogenation, thereby converting the high-boiling point aldehyde compound into corresponding high-boiling point alcohol compound.

In some embodiments, the process further comprises subjecting the high-boiling point aldehyde compound to catalytic hydrogenation, thereby converting the high-boiling point aldehyde compound into corresponding high-boiling point alcohol compound.

In various embodiments, the high-boiling point alcohol compound has a boiling point of at least about 100° C. at atmospheric pressure.

In various embodiments, the present invention provides a process for producing tricyclodecane dialdehyde and/or pentacyclopentadecane dialdehyde, comprising:

a first step of hydroformylating dicyclopentadiene and/or tricyclopentadiene with hydrogen and carbon monoxide in a non-aqueous hydroformylation solvent in the presence of a hydroformylation catalyst, thereby obtaining a non-aqueous hydroformylation product solution comprising tricyclodecane dialdehyde and/or pentacyclopentadecane dialdehyde, the hydroformylation catalyst, and the non-aqueous hydroformylation solvent;

a second step of contacting the non-aqueous hydroformylation product solution with an aqueous extraction solvent to form a biphasic mixture, wherein the aqueous extraction solvent comprises at least one polyalcohol, at least one primary alcohol, and water;

a third step of separating the biphasic mixture of the second step to obtain: (i) a non-aqueous hydroformylation solvent layer, comprising: the hydroformylation catalyst, and the non-aqueous hydroformylation solvent; and (ii) an aqueous extraction solvent layer, comprising: tricyclodecane dialdehyde and/or pentacyclopentadecane dialdehyde, and the aqueous extraction solvent.

In various embodiments, the present invention provides a process for producing tricyclodecane dialdehyde and/or pentacyclopentadecane dialdehyde, comprising:

a first step of hydroformylating dicyclopentadiene and/or tricyclopentadiene with hydrogen and carbon monoxide in a non-aqueous hydroformylation solvent in the presence of a hydroformylation catalyst, thereby obtaining a non-aqueous hydroformylation product solution comprising tricyclodecane dialdehyde and/or pentacyclopentadecane dialdehyde, the hydroformylation catalyst, and the non-aqueous hydroformylation solvent;

a second step of contacting the non-aqueous hydroformylation product solution with an aqueous extraction solvent to form a biphasic mixture, wherein the aqueous extraction solvent comprises at least one polyalcohol, at least one primary alcohol, and water; and a third step of separating the biphasic mixture of the second step to obtain: (i) a non-aqueous hydroformylation solvent layer, comprising: a first portion of the hydroformylation catalyst, and the non-aqueous hydroformylation solvent; and (ii) an aqueous extraction solvent layer comprising tricyclodecane dialdehyde and/or pentacyclopentadecane dialdehyde, the aqueous extraction solvent; and a second portion of the hydroformylation catalyst.

In some embodiments, the aqueous extraction solvent layer further comprises at least one acetal compound. In some embodiments, the hydroformylation catalyst comprises a hydroformylation catalyst component, and a ligand, wherein the hydroformylation catalyst component comprises an active material. In some embodiments, the content (or amount) of the active material in the aqueous extraction solvent layer is less than about 2 ppm.

In some embodiments, the process for producing tricyclodecane dicarbaldehyde and/or pentacyclopentadecane dicarbaldehyde, further comprises an additional step of recovering tricyclodecane dialdehyde and/or pentacyclopentadecane dialdehyde from the aqueous extraction solvent layer.

In some embodiments, the process further comprises an additional step of subjecting the recovered tricyclodecane dialdehyde and/or pentacyclopentadecane dialdehyde to catalytic hydrogenation, thereby converting the tricyclodecane dialdehyde and/or pentacyclodecane dialdehyde into corresponding tricyclodecane dimethanol and/or pentacyclopentadecane dimethanol.

In some embodiments, the process further comprises an additional step of subjecting the aqueous extraction solvent layer to catalytic hydrogenation, thereby converting the tricyclodecane dialdehyde and/or pentacyclodecane dialdehyde into corresponding tricyclodecane dimethanol and/or pentacyclopentadecane dimethanol.

In various embodiments, the present invention provides a process for producing tricyclodecane dimethanol and/or pentacyclopentadecane dimethanol, comprising:

a first step of hydroformylating dicyclopentadiene and/or tricyclopentadiene with hydrogen and carbon monoxide in a non-aqueous hydroformylation solvent in the presence of a hydroformylation catalyst, thereby obtaining a non-aqueous hydroformylation product solution comprising tricyclodecane dialdehyde and/or pentacyclopentadecane dialdehyde, the hydroformylation catalyst, and the non-aqueous hydroformylation solvent;

a second step of contacting the non-aqueous hydroformylation product solution with an aqueous extraction solvent to form a biphasic mixture, wherein the aqueous extraction solvent comprises at least one polyalcohol, at least one primary alcohol, and water;

a third step of separating the biphasic mixture of the second step to obtain: (i) a non-aqueous hydroformylation solvent layer, comprising: the hydroformylation catalyst, and the non-aqueous hydroformylation solvent; and (ii) an aqueous extraction solvent layer, comprising: tricyclodecane dialdehyde and/or pentacyclopentadecane dialdehyde, and the aqueous extraction solvent; and a fourth step of subjecting the tricyclodecane dialdehyde and/or pentacyclopentadecane dialdehyde obtained in the third step to catalytic hydrogenation, thereby converting the tricyclodecane dialdehyde and/or pentacyclodecane dialdehyde into corresponding tricyclodecane dimethanol and/or pentacyclopentadecane dimethanol.

Some embodiments of the present invention can be defined as any of the following numbered paragraphs:

1. A process for separating a high-boiling point aldehyde compound from a non-aqueous hydroformylation product solution, comprising the steps of:
   (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and
   (b) separating the biphasic mixture of step (a) to obtain:
      (i) a non-aqueous hydroformylation solvent layer, comprising: the hydroformylation catalyst, and the non-aqueous hydroformylation solvent; and
      (ii) an aqueous extraction solvent layer, comprising: the high-boiling point aldehyde compound, and the aqueous extraction solvent.

2. The process of paragraph 1, wherein the primary alcohol is a $C_1$-$C_3$ primary alcohol.

3. The process of paragraph 1, wherein the primary alcohol is selected from methanol, ethanol, and n-propanol.

4. The process of paragraph 1, wherein the primary alcohol is selected from methanol and ethanol.

5. The process of paragraph 1, wherein the polyalcohol is selected from the group consisting of a branched polyalcohol, monocyclic polyalcohol, and polycyclic polyalcohol.

6. The process of paragraph 1, wherein the polyalcohol is selected from the group consisting of $C_4$-$C_{20}$ branched polyalcohol, $C_4$-$C_{20}$ monocyclic polyalcohol, and $C_4$-$C_{20}$ polycyclic polyalcohol.

7. The process of paragraph 1, wherein the polyalcohol is a compound of Formula (I):

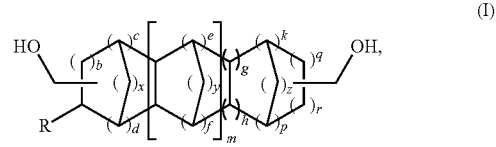

wherein,

R is selected from H and $CH_3$;

x is an integer selected from 0 and 1;

y is an integer selected from 0 and 1;

z is an integer selected from 0 and 1;

b is an integer selected from 0 and 1;
c is an integer selected from 0 and 1;
d is an integer selected from 0 and 1;
e is an integer selected from 0 and 1;
f is an integer selected from 0 and 1;
g is an integer selected from 0 and 1;
h is an integer selected from 0 and 1;
k is an integer selected from 0 and 1;
p is an integer selected from 0 and 1;
q is an integer selected from 0 and 1;
r is an integer selected from 0 and 1; and
m is an integer selected from 0 and 1.

8. The process of paragraph 1, wherein the polyalcohol is selected from the group consisting of 2-methyl-1,3-propanediol; a compound of Formula (II):

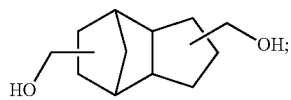

(II)

a compound of Formula (III):

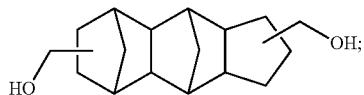

(III)

a compound of Formula (IV):

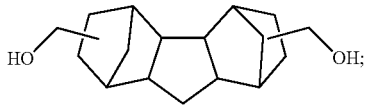

(IV)

and a compound of Formula (V):

(V)

9. The process of paragraph 1, wherein the polyalcohol is selected from the group consisting of 2-methyl-1,3-propanediol; 1,1-cyclohexanedimethanol; 1,2-cyclohexanedimethanol; 1,3-cyclohexanedimethanol; 1,4-cyclohexanedimethanol; 3,8-bis(hydroxymethyl)tricyclo[5.2.1.0$^{2-6}$]decane; 3,9-bis(hydroxymethyl)tricyclo[5.2.1.0$^{2-6}$]decane; 4,8-bis(hydroxymethyl)tricyclo[5.2.1.0$^{2-6}$]decane; 4,9-bis(hydroxymethyl)tricyclo[5.2.1.0$^{2-6}$]decane; 5,8-bis(hydroxymethyl)tricyclo[5.2.1.0$^{2-6}$]decane; 5,9-bis(hydroxymethyl)tricyclo[5.2.1.0$^{2-6}$]decane; 4,10-bis(hydroxymethyl)pentacyclo[6.5.1.1$^{3-6}$.0$^{2-7}$.0$^{9-13}$]pentadecane; 4,11-bis(hydroxymethyl)pentacyclo[6.5.1.1$^{3-6}$.0$^{2-7}$.0$^{9-13}$]pentadecane; 4,12-bis(hydroxymethyl)pentacyclo[6.5.1.1$^{3-6}$.0$^{2-7}$.0$^{9-13}$]pentadecane; 5,10-bis(hydroxymethyl)pentacyclo[6.5.1.1$^{3-6}$.0$^{2-7}$.0$^{9-13}$]pentadecane; 5,11-bis(hydroxymethyl)pentacyclo[6.5.1.1$^{3-6}$.0$^{2-7}$.0$^{9-13}$]pentadecane; 5,12-bis(hydroxymethyl)pentacyclo[6.5.1.1$^{3-6}$.0$^{2-7}$.0$^{9-13}$]pentadecane; 5,12-bis(hydroxymethyl)pentacyclo[9.2.1.1$^{4-7}$.0$^{2-10}$.0$^{3-8}$]pentadecane; 5,13-bis(hydroxymethyl)pentacyclo[9.2.1.1$^{4-7}$.0$^{2-10}$.0$^{3-8}$]pentadecane; 6,12-bis(hydroxymethyl)pentacyclo[9.2.1.1$^{4-7}$.0$^{2-10}$.0$^{3-8}$]pentadecane; and 6,13-bis(hydroxymethyl)pentacyclo[9.2.1.1$^{4-7}$.0$^{2-10}$.0$^{3-8}$]pentadecane.

10. The process of paragraph 1, wherein the polyalcohol is about 10% to about 80% by weight, the primary alcohol is about 10% to about 70% by weight, and the water is about 5% to about 30% by weight, based on the total weight of the aqueous extraction solvent.

11. The process of paragraph 1, wherein the high-boiling point aldehyde compound has a boiling point of at least about 100° C. at atmospheric pressure.

12. The process of paragraph 1, wherein the high-boiling point aldehyde compound is a compound of Formula (VI):

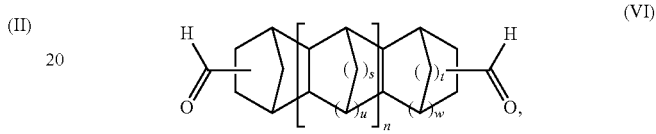

(VI)

wherein,
s is an integer selected from 0 and 1;
t is an integer selected from 0 and 1;
u is an integer selected from 0 and 1;
w is an integer selected from 0 and 1; and
n is an integer selected from 0 and 1.

13. The process of paragraph 1, wherein the high-boiling point aldehyde compound is selected from the group consisting of a compound of Formula (VII):

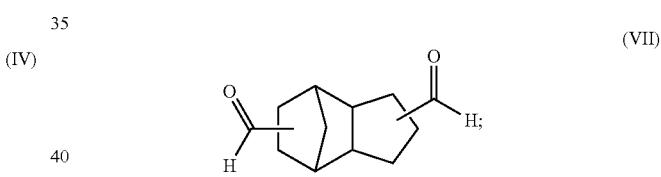

(VII)

a compound of Formula (VIII):

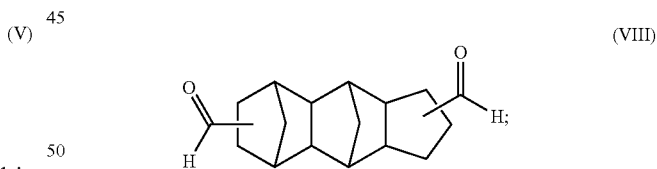

(VIII)

and a compound of Formula (IX):

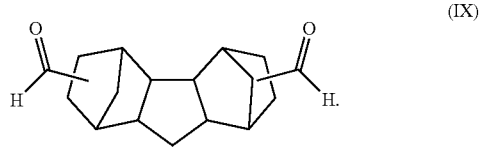

(IX)

14. The process of paragraph 1, wherein the step of contacting the non-aqueous hydroformylation product solution with the aqueous extraction solvent to form the biphasic mixture is performed at a temperature of about 25° C. to about 75° C.

15. The process of paragraph 1, further comprising recovering the hydroformylation catalyst from the non-aqueous hydroformylation solvent layer.

16. The process of paragraph 15, wherein the hydroformylation catalyst comprises a hydroformylation catalyst component and a ligand.

17. The process of paragraph 16, wherein the hydroformylation catalyst component comprises an active material.

18. The process of paragraph 17, wherein the active material is at least one selected from rhodium and cobalt.

19. The process of paragraph 1, further comprising subjecting the aqueous extraction solvent layer to catalytic hydrogenation, thereby converting the high-boiling point aldehyde compound into corresponding high-boiling point alcohol compound.

20. The process of paragraph 1, wherein the aqueous extraction solvent layer has a pH value of less than about 7.

21. The process of paragraph 1, wherein the aqueous extraction solvent layer has a viscosity of less than or equal to about 100 centipoise (cP) at about 25° C.

22. An aldehyde product composition obtained by a process, comprising the steps of:
   (a) contacting a non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises a high-boiling point aldehyde compound, a hydroformylation catalyst, and a non-aqueous hydroformylation solvent; and
   (b) separating the biphasic mixture of step (a) to obtain:
      (i) a non-aqueous hydroformylation solvent layer, comprising: the hydroformylation catalyst, and the non-aqueous hydroformylation solvent; and
      (ii) an aqueous extraction solvent layer, comprising: the aldehyde product composition and the aqueous extraction solvent, wherein the aldehyde product composition comprises the high-boiling point aldehyde compound and an acetal compound.

23. The aldehyde product composition of paragraph 22, wherein a weight ratio of the high-boiling point aldehyde compound to the acetal compound is about 1:0.0001 to about 1:0.05.

The disclosure is further illustrated by the following examples which should not be construed as limiting. The examples are illustrative only, and are not intended to limit, in any manner, any of the aspects described herein. The following examples do not in any way limit the invention.

EXAMPLES

The following examples are not intended to limit the scope of the claims to the invention, but are rather intended to be exemplary of certain embodiments. Any variations in the exemplified processes which occur to the skilled artisan are intended to fall within the scope of the invention.

The invention will be further explained by the following examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1. Procedure for the Hydroformylation Process

The following procedure was performed under an atmosphere of hydrogen and carbon monoxide at 1:1 ratio. 100 g methylcyclohexane, 0.015 g Rh(acac)(CO)$_2$ (Aldrich), and 4.5 g tris-(2,4-di-t-butylphenyl)phosphite (BASF) were mixed together to form a hydroformylation mixture. The hydroformylation mixture was heated to 70° C. for 1.5 hours to dissolve evenly. Once this procedure was completed, the hydroformylation mixture was poured into an autoclave at a pressure of 1 kg/cm$^2$G. After that, the temperature and pressure of the autoclave are increased to 80° C. and 50 kg/cm$^2$G, respectively. 50 g dicyclopentadiene (Zeon) was continuously fed into the autoclave at a rate of 0.83 g/min over a period of 30 minutes using a duplex pump. The reaction was allowed to proceed for 12 hours at a pressure of 50 kg/cm$^2$G. After the reaction was complete, a non-aqueous hydroformylation product solution (175.6 g) was obtained and measured by gas chromatography at room temperature and the results are shown in Table 1.

TABLE 1

| | |
|---|---|
| Dicyclopentadiene Conversion | 100% |
| Tricyclodecane Dialdehyde Yield | 90.2% |
| Tricyclodecane Monoaldehyde Yield | 9.8% |

Example 2. Procedure for the Extraction Process

The non-aqueous hydroformylation product solution (174.5 g) and the aqueous extraction solvent (MPO: 104.4 g, methanol: 35.0 g, water 35.1 g) were mixed at the mass ratio of 1:1 and stirred in a mixer which was held at a temperature of 30° C. After 1 hour stirring, the mixture was poured into a glass extractor and stood for 2 hours and a biphasic mixture (non-aqueous hydroformylation solvent layer (i.e., nonpolar phase) and aqueous extraction solvent layer (i.e., polar phase)) was obtained. The nonpolar phase and polar phase were measured by gas chromatography (Agilent 6980N, column: HP-1 methyl siloxane 30.0 m×0.32 mm×1 um), graphite furnace atomic absorption spectrometry (PerkinElmer Aanalyst 600), and inductively coupled plasma atomic emission spectrometer (Agilent), and the results are shown in Table 2.

TABLE 2

| Nonpolar Phase | Weight (98.8 g) |
|---|---|
| Tricyclodecane Dialdehyde Content$^a$ | 1.50 wt % |
| Tricyclodecane Monoaldehyde Content$^a$ | 3.68 wt % |
| Rhodium Content$^b$ | 61 ppm |
| Ligand Content$^c$ | 4.5 wt % |
| Polar Phase | Weight (252.0 g) |
| Tricyclodecane Dialdehyde Content$^a$ | 24.27 wt % |
| Tricyclodecane Monoaldehyde Content$^a$ | 1.59 wt % |

TABLE 2-continued

| | |
|---|---|
| Rhodium Content[b] | 191 ppb |
| Ligand Content[c] | 273 ppm |

[a]Measured by gas chromatography.
[b]Measured by graphite furnace atomic absorption spectrometry.
[c]Measured by inductively coupled plasma atomic emission spectrometer.

Calculation of Extraction Efficiency (%).
The Extraction Efficiency (%) is calculated as follows:

Extraction Efficiency (%)=[($A_H$×$W_H$)/(($A_H$×$W_H$)+($A_L$×$W_L$))]×100

$A_L$: the concentration of tricyclodecane dialdehyde in the nonpolar phase
$W_L$: the weight of the nonpolar phase
$A_H$: the concentration of tricyclodecane dialdehyde in the polar phase
$W_H$: the weight of the polar phase
The concentration of tricyclodecane dialdehyde is measured by gas chromatography.
For example, tricyclodecane dialdehyde is a high-boiling point aldehyde compound; the nonpolar phase is the non-aqueous hydroformylation solvent layer; and the polar phase is the aqueous extraction solvent layer.

Calculation of Rhodium (Rh) Loss (ppb).
The Rhodium (Rh) Loss (ppb) is calculated as follows:
Rh Loss=Rh content (amount) in polar phase of the biphasic mixture.
The Rh content is measured by a graphite furnace atomic absorption spectrometry.
For example, rhodium is the active material; and the polar phase is the aqueous extraction solvent layer.

Calculation of Acetal Compound Content (%).
The Acetal Compound Content (%) is calculated as follows:

Acetal Compound Content (%)=(Weight of Acetal Compound in Polar Phase/Weight of Tricyclodecane Dialdehyde in Polar Phase)×100

The weight of the acetal compound and the tricyclodecane dialdehyde are measured by gas chromatography at 25° C. after the biphasic mixture is allowed to stand for 1 hour.
For example, tricyclodecane dialdehyde is a high-boiling point aldehyde compound; and the polar phase is the aqueous extraction solvent layer.

Examples 3a-3h. Extraction Solvents

A non-aqueous hydroformylation product solution prepared according to Example 1—Procedure for the Hydroformylation Process was extracted using various extraction solvents as shown in Table 3.

TABLE 3

| Example | Extraction Solvent (weight ratio) | Extraction Efficiency (%) | Rh Loss (ppb) | Acetal Compound Content (wt %) | TCDDA:Acetal (weight ratio) | Kp |
|---|---|---|---|---|---|---|
| 3a | MPO:MeOH:H₂O (1:7:2) | 98.00 | 181 | 0.45 | 1:0.018 | 14.3 |
| 3b | TCDDM:MeOH:H₂O (1:7:2) | 98.30 | 334 | 0.03 | 1:0.0012 | 19.2 |
| 3c | CHDM:MeOH:H₂O (1:6:3) | 97.80 | 338 | 0.1 | 1:0.004 | 16.38 |
| 3d | MPO:EtOH:H₂O (1:6:3) | 98.40 | 345 | 0.34 | 1:0.0136 | 17.9 |
| 3e | Ethylene glycol:H₂O (8:2) | 81 | 347 | 0.64 | 1:0.0256 | 8.22 |
| 3f | Propylene glycol:H₂O (8:2) | 83 | 479 | 0.64 | 1:0.0256 | 8.86 |
| 3g | MeOH:H₂O (8:2) | 70 | 1210 | 0.71 | 1:0.0284 | 4.16 |
| 3h | Ethylene glycol | 27.4 | 630 | Not Measured | — | 0.27 |
| 3i | Propylene glycol | 78.6 | 930 | Not Measured | — | 4.5 |

In the present invention, the partition coefficient, Kp=(concentration of high-boiling point aldehyde compound in polar phase/concentration of high-boiling point aldehyde compound in nonpolar phase). For example, Kp=(concentration of TCDDA in polar phase/concentration of TCDDA in nonpolar phase).

For example, TCDDA is the high-boiling point aldehyde compound; the polar phase is the aqueous extraction solvent layer; and the nonpolar phase is the non-aqueous hydroformylation solvent layer.

The Extraction Solvents (Examples 3a-3d) of Table 3 are each an embodiment of an extraction solvent (i.e., aqueous extraction solvent) of the present invention. The Extraction Solvents (Examples 3e-3i) of Table 3 are not extraction solvents of the present invention and are provided for comparative purposes.

Compared to Example 3e-3g, embodiments of the present invention can provide high extractive efficiency, low amount of rhodium loss and low yield amount of acetal compound. Compared to Example 3h-3i, embodiments of the present invention also can provide high extraction efficiency and low amount of rhodium loss. The amount of acetal compound in Examples 3h-3i was not measured.

Furthermore, compared to the examples and results shown in Table 2 of U.S. Pat. No. 6,365,782 B1, the embodiments of the present invention can provide higher partition coefficient (Kp) values and are therefore better suited for industrial use.

Examples 4a-4c. Extraction Temperature

A non-aqueous hydroformylation product solution prepared according to Example 1—Procedure for the Hydroformylation Process was extracted using the Extraction Solvent: MPO:MeOH:H₂O (7:1:2) at various temperatures as shown in Table 4. The Extraction Solvent: MPO:MeOH:H₂O (7:1:2) is an embodiment of an extraction solvent (i.e., aqueous extraction solvent) of the present invention.

TABLE 4

| Example | Temperature (° C.) | Extraction Efficiency (%) | Rh Loss (ppb) | Acetal Compound Content (wt %) | TCDDA: Acetal (Weight Ratio) |
|---|---|---|---|---|---|
| 4a | 30 | 98.0 | 209 | 0.08 | 1:0.0032 |
| 4b | 50 | 96.4 | 191 | 0.69 | 1:0.0276 |
| 4c | 70 | 91.7 | 310 | 0.96 | 1:0.0384 |

Examples 5a-5d. Extraction Solvents

A non-aqueous hydroformylation product solution prepared according to Example 1—Procedure for the Hydroformylation Process was extracted using the various extraction solvents as shown in Table 5.

TABLE 5

| Example | Extraction Solvent (weight ratio) | Extraction Efficiency (%) | Rh Loss (ppb) | Acetal Compound Content (wt %) | TCDDA: Acetal (weight ratio) | Kp |
|---|---|---|---|---|---|---|
| 5a | MPO:MeOH:$H_2O$ (8:1.5:0.5) | 98.69 | 354 | 0.12 | 1:0.005 | 22.6 |
| 5b | MPO:MeOH:$H_2O$ (7:1:2) | 98.20 | 186 | 0.36 | 1:0.0144 | 17.3 |
| 5c | MPO:MeOH:$H_2O$ (7:2:1) | 98.33 | 216 | 0.18 | 1:0.007 | 18.4 |
| 5d | MPO:MeOH:$H_2O$ (6:2:2) | 98.00 | 192 | 0.37 | 1:0.0148 | 15.96 |
| 5e | MPO:MeOH:$H_2O$ (3:5:2) | 97.9 | 177 | 0.37 | 1:0.0148 | 17.9 |
| 5f | MPO:MeOH:$H_2O$ (1:7:2) | 98.00 | 181 | 0.45 | 1:0.018 | 14.3 |

The Extraction Solvents (Examples 5a-5f) of Table 5 are each an embodiment of an extraction solvent (i.e., aqueous extraction solvent) of the present invention.

Examples 6a-6d. Extraction Solvent Vs. Aldehyde Product Composition Viscosity

A non-aqueous hydroformylation product solution prepared according to Example 1—Procedure for the Hydroformylation Process was extracted using the various extraction solvents as shown in Table 6. The viscosity of the aldehyde product composition was measured at 25° C. using a viscometer (Brookfield, type E HADV-I+CP; rotor LV-4).

TABLE 6

| Example | Weight ratio of extraction solvent (MPO:MeOH:$H_2O$) | Viscosity at 25° C. (cP) |
|---|---|---|
| 6a | 8:0:2 | 273 |
| 6b | 8:1:1 | 197 |
| 6c | 7:2:1 | 97 |
| 6d | 6:2:2 | 56 |

The Extraction Solvents (Examples 6b-6d) of Table 6 are each an embodiment of an extraction solvent (i.e., aqueous extraction solvent) of the present invention. The Extraction Solvent (Examples 6a) of Table 6 is not an extraction solvent of the present invention and is provided for comparative purposes. According to the results shown in Table 6, the viscosity is markedly reduced by using an extraction solvent (i.e., aqueous extraction solvent) of the present invention.

The various processes and techniques described above provide a number of ways to carry out the application. Of course, it is to be understood that not necessarily all objectives or advantages described can be achieved in accordance with any particular embodiment described herein. Thus, for example, those skilled in the art will recognize that the processes can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform processes in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents and other publications identified in the specification and examples are expressly incorporated herein by reference for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail. These patents and other publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

Although particular embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A process for separating a high-boiling point aldehyde compound from a non-aqueous hydroformylation product solution, comprising the steps of:
    (a) contacting the non-aqueous hydroformylation product solution with an aqueous extraction solvent to form a biphasic mixture, wherein the aqueous extraction solvent comprises at least one polyalcohol, at least one primary alcohol, and water; and wherein the non-aqueous hydroformylation product solution comprises the high-boiling point aldehyde compound, a hydroformylation catalyst, and a non-aqueous hydroformylation solvent; and
    (b) separating the biphasic mixture of step (a) to obtain:
        (i) a non-aqueous hydroformylation solvent layer, comprising: the hydroformylation catalyst, and the non-aqueous hydroformylation solvent; and
        (ii) an aqueous extraction solvent layer, comprising: the high-boiling point aldehyde compound, and the aqueous extraction solvent.

2. The process of claim 1, wherein the primary alcohol is a $C_1$-$C_3$ primary alcohol.

3. The process of claim 1, wherein the primary alcohol is selected from methanol, ethanol, and n-propanol.

4. The process of claim 1, wherein the primary alcohol is selected from methanol and ethanol.

5. The process of claim 1, wherein the polyalcohol is selected from the group consisting of a branched polyalcohol, monocyclic polyalcohol, and polycyclic polyalcohol.

6. The process of claim 1, wherein the polyalcohol is selected from the group consisting of $C_4$-$C_{20}$ branched polyalcohol, $C_4$-$C_{20}$ monocyclic polyalcohol, and $C_4$-$C_{20}$ polycyclic polyalcohol.

7. The process of claim 1, wherein the polyalcohol is a compound of Formula (I):

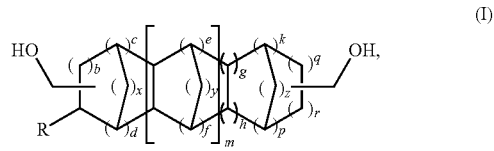

wherein,
R is selected from H and $CH_3$;
x is an integer selected from 0 and 1;
y is an integer selected from 0 and 1;
z is an integer selected from 0 and 1;
b is an integer selected from 0 and 1;
c is an integer selected from 0 and 1;
d is an integer selected from 0 and 1;
e is an integer selected from 0 and 1;
f is an integer selected from 0 and 1;
g is an integer selected from 0 and 1;
h is an integer selected from 0 and 1;
k is an integer selected from 0 and 1;
p is an integer selected from 0 and 1;
q is an integer selected from 0 and 1;
r is an integer selected from 0 and 1; and
m is an integer selected from 0 and 1.

8. The process of claim 1, wherein the polyalcohol is selected from the group consisting of 2-methyl-1,3-propanediol; a compound of Formula (II):

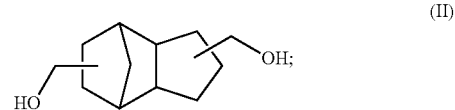

a compound of Formula (III):

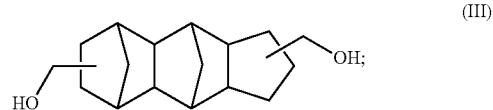

a compound of Formula (IV):

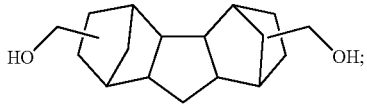

and a compound of Formula (V):

9. The process of claim 1, wherein the polyalcohol is selected from the group consisting of 2-methyl-1,3-propanediol; 1,1-cyclohexanedimethanol; 1,2-cyclohexanedimethanol; 1,3-cyclohexanedimethanol; 1,4-cyclohexanedimethanol; 3,8-bis(hydroxymethyl)tricyclo[5.2.1.0$^{2-6}$]decane; 3,9-bis(hydroxymethyl)tricyclo[5.2.1.0$^{2-6}$]decane; 4,8-bis(hydroxymethyl)tricyclo[5.2.1.0$^{2-6}$]decane; 4,9-bis(hydroxymethyl)tricyclo[5.2.1.0$^{2-6}$]decane; 5,8-bis(hydroxymethyl)tricyclo[5.2.1.0$^{2-6}$]decane; 5,9-bis(hydroxymethyl)tricyclo[5.2.1.0$^{2-6}$]decane; 4,10-bis(hydroxymethyl)pentacyclo[6.5.1.1$^{3-6}$.0$^{2-7}$.0$^{9-13}$]pentadecane; 4,11-bis(hydroxymethyl)pentacyclo[6.5.1.1$^{3-6}$.0$^{2-7}$.0$^{9-13}$]pentadecane; 4,12-bis(hydroxymethyl)pentacyclo[6.5.1.1$^{3-6}$.0$^{2-7}$.0$^{9-13}$]pentadecane; 5,10-bis(hydroxymethyl)pentacyclo[6.5.1.1$^{3-6}$.0$^{2-7}$.0$^{9-13}$]pentadecane; 5,11-bis(hydroxymethyl)pentacyclo[6.5.1.1$^{3-6}$.0$^{2-7}$.0$^{9-13}$]pentadecane; 5,12-bis(hydroxymethyl)pentacyclo[6.5.1.1$^{3-6}$.0$^{2-7}$.0$^{9-13}$]pentadecane; 5,12-bis(hydroxymethyl)pentacyclo[9.2.1.1$^{4-7}$.0$^{2-10}$.0$^{3-8}$]pentadecane; 5,13-bis(hydroxymethyl)pentacyclo[9.2.1.1$^{4-7}$.0$^{2-10}$.0$^{3-8}$]pentadecane; 6,12-bis(hydroxymethyl)pentacyclo[9.2.1.1$^{4-7}$.0$^{2-10}$.0$^{3-8}$]pentadecane; and 6,13-bis(hydroxymethyl)pentacyclo[9.2.1.1$^{4-7}$.0$^{2-10}$.0$^{3-8}$]pentadecane.

10. The process of claim 1, wherein the polyalcohol is about 10% to about 80% by weight, the primary alcohol is about 10% to about 70% by weight, and the water is about 5% to about 30% by weight, based on the total weight of the aqueous extraction solvent.

11. The process of claim 1, wherein the high-boiling point aldehyde compound has a boiling point of at least about 100° C. at atmospheric pressure.

12. The process of claim 1, wherein the high-boiling point aldehyde compound is a compound of Formula (VI):

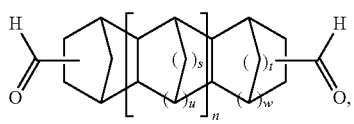

wherein,
s is an integer selected from 0 and 1;
t is an integer selected from 0 and 1;
u is an integer selected from 0 and 1;
w is an integer selected from 0 and 1; and
n is an integer selected from 0 and 1.

13. The process of claim 1, wherein the high-boiling point aldehyde compound is selected from the group consisting of a compound of Formula (VII):

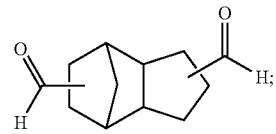

a compound of Formula (VIII):

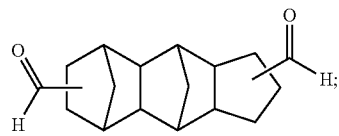

and a compound of Formula (IX):

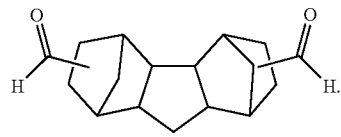

14. The process of claim 1, wherein the step of contacting the non-aqueous hydroformylation product solution with the aqueous extraction solvent to form the biphasic mixture is performed at a temperature of about 25° C. to about 75° C.

15. The process of claim 1, further comprising recovering the hydroformylation catalyst from the non-aqueous hydroformylation solvent layer.

16. The process of claim 15, wherein the hydroformylation catalyst comprises a hydroformylation catalyst component and a ligand.

17. The process of claim 16, wherein the hydroformylation catalyst component comprises an active material.

18. The process of claim 17, wherein the active material is at least one selected from rhodium and cobalt.

19. The process of claim 1, further comprising subjecting the aqueous extraction solvent layer to catalytic hydrogenation, thereby converting the high-boiling point aldehyde compound into corresponding high-boiling point alcohol compound.

20. The process of claim 1, wherein the aqueous extraction solvent layer has a pH value of less than about 7.

21. The process of claim 1, wherein the aqueous extraction solvent layer has a viscosity of less than or equal to about 100 centipoise (cP) at about 25° C.

* * * * *